(12) United States Patent
Kónya et al.

(10) Patent No.: US 6,517,550 B1
(45) Date of Patent: Feb. 11, 2003

(54) FOREIGN BODY RETRIEVAL DEVICE

(75) Inventors: András Kónya, Houston, TX (US); Kenneth C. Wright, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/496,482

(22) Filed: Feb. 2, 2000

(51) Int. Cl.⁷ .............................................. A61B 17/00
(52) U.S. Cl. ..................................................... 606/113
(58) Field of Search ............................... 606/113, 114, 606/127, 79, 110

(56) References Cited

U.S. PATENT DOCUMENTS

| | | |
|---|---|---|
| 3,791,387 A | 2/1974 | Itoh |
| 3,828,790 A | 8/1974 | Curtiss et al. |
| 3,835,859 A * | 9/1974 | Roberts et al. ............. 128/305 |
| 3,910,279 A | 10/1975 | Okada et al. |
| 3,955,578 A | 5/1976 | Chamness et al. |
| 4,046,149 A * | 9/1977 | Komiya ...................... 128/328 |
| 4,493,320 A | 1/1985 | Treat |
| 4,718,419 A | 1/1988 | Okada |
| 5,108,406 A | 4/1992 | Lee |
| 5,163,938 A | 11/1992 | Kambara et al. |
| 5,171,233 A | 12/1992 | Amplatz et al. |
| 5,171,314 A | 12/1992 | Dulebohn |
| 5,192,286 A | 3/1993 | Phan et al. |
| 5,281,238 A | 1/1994 | Chin et al. |
| 5,342,371 A | 8/1994 | Welter et al. |
| 5,376,094 A | 12/1994 | Kline |
| 5,387,219 A | 2/1995 | Rappe |
| 5,417,684 A | 5/1995 | Jackson et al. |
| 5,535,759 A | 7/1996 | Wilk |
| 5,562,678 A | 10/1996 | Booker |
| 5,588,442 A | 12/1996 | Scovil et al. |
| 5,643,281 A | 7/1997 | Suhocki et al. |
| 5,681,324 A | 10/1997 | Kammerer et al. |
| 5,741,271 A | 4/1998 | Nakao et al. |
| 5,810,852 A | 9/1998 | Greenberg et al. |
| 5,824,044 A | 10/1998 | Quiachon et al. |
| 5,868,698 A | 2/1999 | Rowland et al. |
| 5,868,754 A | 2/1999 | Levine et al. |
| 5,873,876 A | 2/1999 | Christy |
| 5,893,859 A | 4/1999 | Marin et al. |
| 5,895,398 A * | 4/1999 | Wensel et al. ............... 606/159 |
| 5,989,264 A * | 11/1999 | Wright ........................ 606/113 |
| 6,017,340 A | 1/2000 | Cassidy et al. |
| 2002/0002376 A1 * | 1/2002 | Gannoe et al. ............. 606/167 |

FOREIGN PATENT DOCUMENTS

EP            0123175          10/1984

OTHER PUBLICATIONS

Curry, "Recovery of detached intravascular catheter or guide wire fragments," *Am. J. Roentgenol. Radium Ther. Nucl. Med.*, 105(4):894–896, 1969.

(List continued on next page.)

*Primary Examiner*—Eduardo C. Robert
(74) *Attorney, Agent, or Firm*—Fulbright & Jaworski L.L.P.

(57) ABSTRACT

A retrieval device or snare for grasping foreign articles and retrieving them from the body of a patient. The retrieval device includes a catheter open at both ends such that it may be advanced along a guidewire. The distal end of a wire is attached to the first catheter near an opening system within the catheter. The opening system may be a slot or a pair of holes. A portion of the wire is oriented external of the catheter. Manipulation of the proximal end of the wire causes a portion of the wire to form a loop external of the catheter. The catheter may be tapered, as may be the wire. A reinforcing material may be attached to the portion of the wire that forms the loop. Another reinforcing material may also be attached to the proximal portion of the wire in order to stiffen the wire and improve its pushability. A guidewire may be inserted into a patient and maneuvered to an appropriate location within the patient, the catheter may be advanced over the guidewire, the wire attached to the catheter may be manipulated to capture a foreign body with the loop, and the catheter and foreign body may be withdrawn from the patient.

47 Claims, 8 Drawing Sheets

OTHER PUBLICATIONS

Dotter et al., "Transluminal extraction of catheter and guide fragments from the heart and great vessels; 29 collected case," *Am. J. Roentgenol. Radium Ther. Nucl. Med.*, 111(3):467–472, 1971.

Fisher and Ferreyro, "Evaluation of current techniques for nonsurgical removal of intravascular latrogenic foreign bodies," *Am. J. Roentgenol.*, 130:541–548, 1978.

Furui et al., "Intravascular foreign bodies: loop–snare retrieval system with a three–lumen catheter," *Radiology*, 182(1):283–284, 1992.

Smith, "An improved method for Intra–arterial foreign body retrieval," *Radiology*, 145:539, 1982.

Thomas et al., "Non–surgical retrieval of a broken segment of steel spring guide from the right atrium and inferior Vena Cava," *Circulation*, 30:106–108, 1964.

Uflacker et al., "Intravascular foreign bodies: percutaneous retrieval," *Radiology*, 160:731–735, 1986.

Galal et al., "Problems encountered during introduction of Gianturco coils for transcatheter occlusion of the patent arterial duct," *Eur. Heart J.*, 18:625–630, 1997.

Ing and Bierman, "Percutaneous transcatheter coil occlusion of the patent ductus arteriosus aided by the nitinol snare: further observations," *Cardiovasc. Intervent. Radiol.*, 18:222–226, 1995.

Lipton et al., "Percutaneous retrieval of two Wallstent endoprostheses from the hear through a single jugular sheath," *JVIR*, 6:469–472, 1995.

Siegel and Robertson, "Percutaneous transfemoral retrieval of a free–floating Titanium Greenfield filter with an Amplatz goose neck snare," *JVIR*, 4:565–568, 1993.

Sommer et al., "Use of preformed nitinol snare to improve transcatheter coil delivery in occlusion of patent ductus arteriosus," *American J of Cardiology*, 74:836–839, 1994.

Bett et al., "Plastic catheter embolism to the right heart a technique of non–surgical removal," *Med. J. of Aust.*, 854–856, 1971.

Bloomfield, "The nonsurgical retrieval of intracardiac foreign bodies—an international survey," *Cathet. Cardiovasc. Diagn.*, 4:1–14, 1978.

David J. G. Ferguson, "Removal of an intracardiac foreign body without thoracotomy," *Hawaii Med. Jour.*, 32:321–323, 1973.

Geraci and Selman, "Pulmonary artery catheter emboli: successful nonsurgical removal," *Annals Int. Med.*, 78:353–356.

Hyman, "An improved snare catheter for retrieving embolized fragments of polyethylene tubing," *Chest*, 62:98–99, 1972.

File history for U.S. Patent No. 5,342,371.

File history for U.S. Patent No. 5,171,233.

* cited by examiner

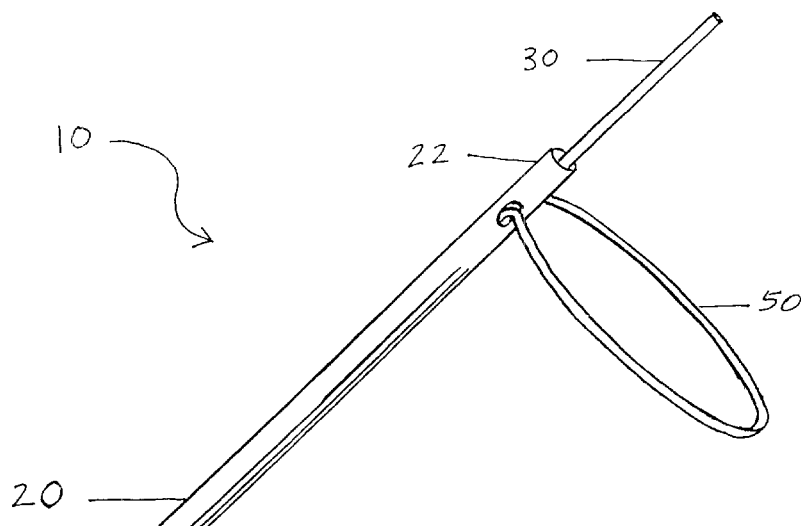
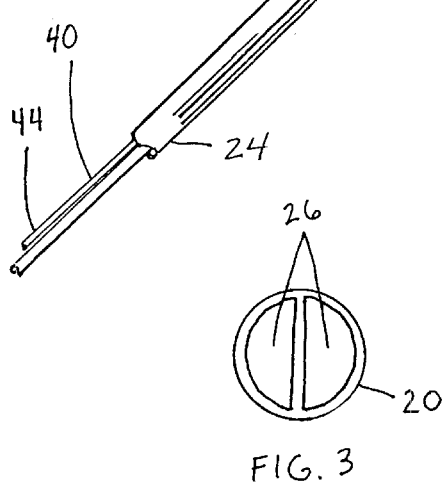
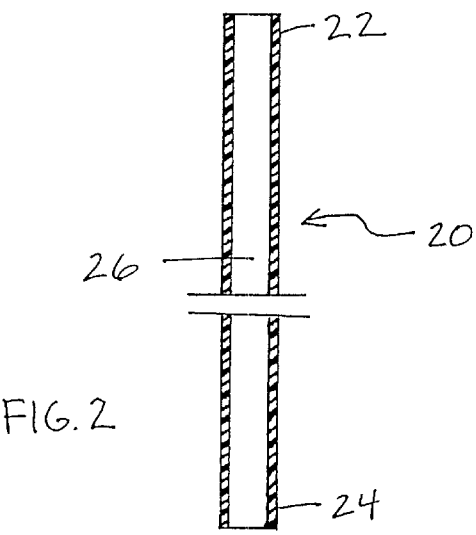
FIG. 1
FIG. 2
FIG. 3

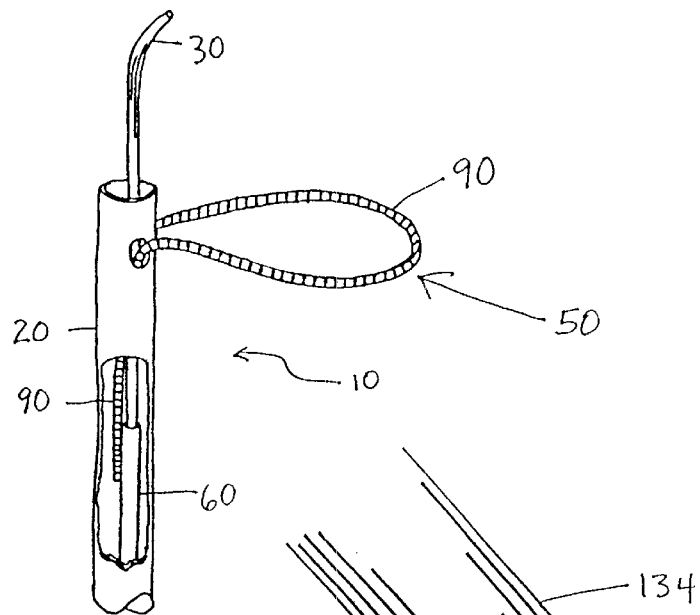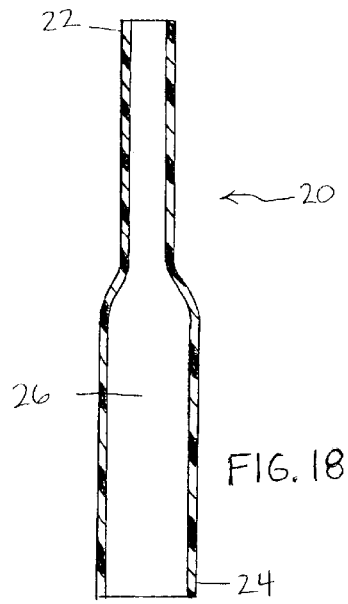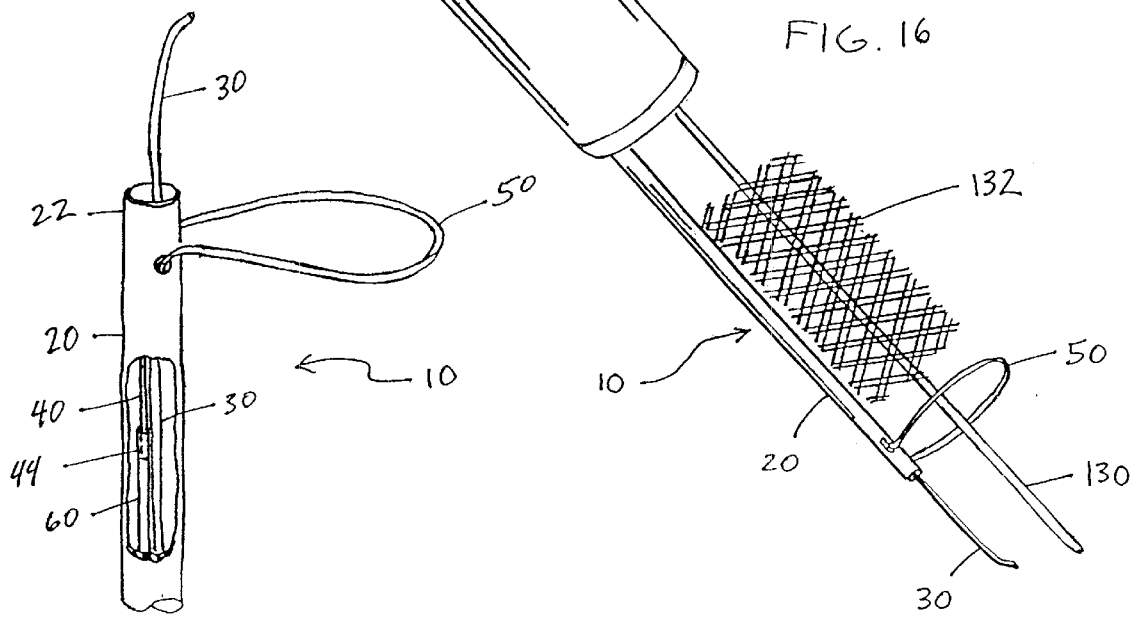

FOREIGN BODY RETRIEVAL DEVICE

BACKGROUND OF THE INVENTION

1. Field of the Invention

The present invention relates generally to the field of medical instruments for retrieving foreign articles from patients. More particularly, it concerns an apparatus for use as a snare or foreign body retrieval device that is guidewire-compatible and includes a continuously-adjustable, laterally-oriented loop.

2. Description of Related Art

During medical procedures which utilize catheters, guidewires, pacemaker leads, or other medical devices, a portion of the device can sometimes break off and be left within the patient. The detached portion may then travel within the patient's vascular system and come to rest in a luminal organ, vein or artery, and usually at a branching point or in the heart. Leaving these foreign bodies within the patient can be quite harmful, and may result in complications like sepsis, perforation, thrombosis, arrhythmias, myocardial necrosis, or even death. Therefore, it is necessary and urgent to remove the foreign body from the patient.

Similarly, several interventional radiological procedures involve implantation of different devices within the body. Recently, embolization coils, stents and vena cava filters, among others, have been frequently used. Misplacement and/or dislodgment of these devices may result in serious consequences and necessitate their removal (Galal et al., *Eur. Heart J.*, 1997; Ing and Bierman, *Cardiovasc. Intervent. Radiol.*, 1995; Siegel and Robertson, *JVIR*, 1993; Lipton, *JVIR*, 1995).

The percutaneous removal of foreign bodies or devices has become acceptable because it is relatively easy and safe. However, current devices possess certain shortcomings that inhibit their ease and range of use.

The Amplatz "Goose Neck" snare, commercially available from Microvena Corporation of White Bear Lake, MN, is currently the most popular snare. Described in U.S. Pat. No. 5,171,233 to Amplatz et al. (1992), the Amplatz snare consists of a superelastic wire that is bent in half. The two wire segments created as a result of the bend are bonded together to eliminate the possibility of moving the segments relative to each other. A loop is fashioned at the location of the bend. The loop is bent at its proximal end (i.e., the end of the loop closest to the operator) such that the loop is oriented at an angle to the bonded wire segments. Because the wire segments are bonded together to prevent the relative movement of either, the size of the loop is fixed.

In order to operate the Amplatz snare, the loop is constrained (pinched) and inserted into a catheter. Once positioned in the patient, to utilize the loop, the position of the catheter is maintained, and the folded wire is pushed until the loop is fully extended beyond the tip of the catheter. It then returns to its unconstrained configuration. Prior to being completely extended beyond the tip of the catheter, the loop will remained constrained and useless.

After the loop is formed, the Amplatz snare may be manipulated until the loop passes over the foreign body to be retrieved. Then, by maintaining the position of the folded wire, the catheter may be advanced over the bonded segments and the loop until the foreign body is firmly wedged between the distal end of the loop and the catheter. This process may also be achieved by holding the catheter steady and withdrawing the bonded wire segments, or both may be manipulated at once. The snare may then be removed from the patient along with the laterally-oriented foreign body.

A purported advantage of the bonded wire segments and fixed loop of the Amplatz snare is that the operator need only utilize one hand to form the loop, in contrast to other snares in which the relative movement of the two wire halves may be required in order to form a useful loop. (See, e.g., the snare disclosed in Bett et al., *Med. J Aust.*, 1971)

The fixed nature of the loop of the Amplatz snare, however, poses certain shortcomings. For example, because the loop is fixed, having only one or two snare sizes may not be feasible to efficiently remove foreign bodies of all sizes in the least disruptive manner to the patient. Obviously, while having a snare with a relatively large loop may be useful for retrieving correspondingly large foreign bodies in sufficiently sized vessels or structures, a patient could be traumatized by retrieving a more diminutively-sized foreign body with the same snare. Specifically, it would not be beneficial to the patient to retrieve a small foreign body lodged in a small vessel or structure with an Amplatz snare having a loop that is larger than the size of the vessel. The vessel or structure could be traumatized by the pressure the loop would exert on the wall thereof during the procedure. As a result, it is not possible to feasibly utilize one or two Amplatz snares for the retrieval of foreign bodies of virtually all sizes.

Further, as a result of the fixed nature of the loop and the fact that it must be extended beyond the tip of the catheter before it is formed and operational, if a foreign body were positioned in a way that made it more feasible to surround it by withdrawing the loop toward the operator rather than by advancing the loop away from him or her, the tip of the catheter would need to be positioned distally of the distal end of the foreign body prior to forming the loop. As a result, the vessel or structure would need to possess a sufficient amount of space distal of the foreign body in which the constrained loop could be extended during its formation. If such space did not exist, such as at a branch or bifurcation, the Amplatz snare would be useless in that application.

Another shortcoming of the Amplatz snare is that prior to removing it, the foreign body must be pinched or wedged between the distal end of the loop and the distal tip of the catheter. As a result, in cases in which the foreign body is straight or slightly bent, the foreign body will be oriented transversely to the catheter as it is being withdrawn. Consequently, the wall of the vessel or structure from which it is removed may be traumatized by the laterally-oriented foreign body scraping against it as the foreign body is extracted. For the same reason, negotiating tortuous passageways may be difficult, and the foreign body may become caught or wedged in a passageway and require surgical removal.

Yet another shortcoming of the Amplatz snare is that it is not guidewire compatible. The use of a guidewire is neither disclosed nor suggested by the Amplatz patent. Thus, the catheter in which the folded wire is housed must be used to guide the snare to its desired location. Further, the use of a guidewire with the Amplatz snare would only add to its bulk since a larger delivery catheter would be needed in order to accommodate the two twisted wire segments bonded together and the guidewire.

The surgical snare disclosed in U.S. Pat. No. 5,342,371 to Welter et al. (1994) (commercially available from Cook Inc., Bloomington, Ind.) (the "Welter snare") suffers from some of the same shortcomings as the Amplatz snare, but addresses one of them. The Welter consists of an elongated member in which two longitudinally spaced-apart ports are provided. A stainless steel wire is threaded out of one of the ports, helically wrapped around the elongated member, and threaded back into the member through the other port, thereby forming a collapsed, stainless steel helical snare loop external of the member. The distal end of the stainless steel wire is attached to the distal end of the member. The stainless steel helical snare loop may be opened and closed by manipulating a sliding handle affixed to the proximal end of the member. By attaching the distal end of the stainless steel wire to the distal end of the elongated member, the Welter snare addresses the problem recognized in the Amplatz patent of having to move one end of the stainless steel wire forming the helical snare loop relative to the other by fixing the position of the distal end of the wire, instead of by bending the wire and bonding the two wire segments. As a result, the stainless steel helical snare loop of the Welter snare may not only be operated with one hand, a goal achieved by the bonded wire segments of the Amplatz snare, but may also be continuously adjusted.

The member is closed at its distal end and, as a result, the Welter snare is not guidewire compatible. As such, it suffers from the same shortcomings in this regard as does the Amplatz snare. Further, the use of a guidewire is not suggested in the Welter patent because the function of a guidewire—namely control—is taught as being accomplished by a stainless steel wire braid embedded as a torque control member in the wall of the member. This embedded stainless steel wire braid purportedly facilitates directional control of the member through the vascular system of the patient. The wire braid is embedded in the wall of the member during the extrusion of the member.

The Welter patent discloses that the ports in the elongated member are spaced longitudinally apart from each other. The stainless steel wire threaded through the ports, which forms the helical snare loop, is wrapped around the elongated member such that the stainless steel loop may be formed and operated without it being laterally deformed or kinked. In this regard, the Welter patent recognizes the shortcomings of loops that may kink during use, and appears to address this problem by ensuring the formation of a helical snare loop (i.e., one that is not laterally deformed) through the longitudinal spacing of the ports in the member and the orientation of the stainless steel wire between the ports.

A shortcoming of this design, however, is the fact that the stainless steel wire occupies space around the circumference of the member during its introduction into and movement throughout the body of the patient. As a result, the stainless steel wire could disrupt fluid flow, or even cause damage to the vessel or luminal organ in which it is placed if, for example, the vessel or luminal organ is irregular in shape due to the presence of plaque, etc. Additionally, as the stainless steel helical snare loop is opened, utilized, and closed, it occupies space within the patient along the entire length of the member located between the two ports. Consequently, the vessel or luminal structure in which the Welter snare is utilized is subject to the potential damage just described along its length that corresponds to the length of the member between the two ports. Similarly, as the stainless steel helical snare loop is operated, the potential for the disruption of fluid flow increases because the size of the amount of stainless steel wire present in the vessel or luminal organ increases.

Another snare is disclosed in an article from The Medical Journal of Australia ("the Australian snare") and includes a catheter having two small holes in it, and a nylon fishing line threaded through the holes (Bett et al, *Med. J. Aust.*, 1971). The ends of the nylon line extend beyond the proximal hub of the catheter, the hub being formed from a short collar of polyurethane tubing. The location of the holes is not clear from the article. The Australian snare is also reviewed in another article that depicts the holes in the snare as being longitudinally spaced-apart in FIG. 4 thereof (Bloomfield, *Cathet. Cardiovasc. Diagn.*, 1978).

Whatever the position of the holes in the Australian snare, it suffers from one shortcoming recognized in the Amplatz patent—the need for the relative movement of the ends of the nylon line to form a useful loop. Although an operator could hold the two ends of the nylon line together and advance both at the same type in attempting to form the loop, the rigidity of the nylon line could pose certain problems. For example, it is likely that the nylon line, having no more rigidity than that of fishing line, would be difficult to smoothly advance through the holes in the catheter. (The limpness of the line is depicted in FIG. 4 of the Bloomfield article.) That is, the relatively limp nylon line would likely have a tendency to buckle as the loop is formed. This would likely be especially true if both ends of the line were held together and advanced simultaneously. Another problem posed by the relative limpness of the nylon line is that if the position of the loop formed was disrupted by either the foreign body or a portion of the patient's anatomy, the lack of rigidity of the nylon line could prevent the operator from readily re-achieving an operable configuration of the misshapen loop.

The problems pointed out with the foregoing snares are not intended to be exhaustive but rather are among many that tend to impair the effectiveness of previously known snares. Other noteworthy problems may also exist; however, those presented above should be sufficient to demonstrate that previous techniques appearing in the art have not been altogether satisfactory, particularly in providing a simply-constructed snare that is easily-maneuverable and capable of grasping articles in a reliable and minimally-invasive fashion.

SUMMARY OF THE INVENTION

In one respect, the invention is a retrieval device that includes, but is not limited to, a first catheter that has a distal end, a proximal end, a lumen system configured to accept at least one wire such that the at least one wire may extend beyond either end of the first catheter, and an opening system through which a loop may be formed; and a wire that has a distal end attached to the first catheter, and a proximal end. The proximal end of the wire may be manipulated to cause a portion of the wire to form a loop external of the first catheter. The loop is capable of grasping foreign bodies within a patient.

The retrieval device may also include, but is not limited to, a guidewire that is configured to be placed within the lumen system. The opening system may include first and second openings. The first opening may be spaced from the distal end of the first catheter by a first distance, the second opening may be spaced from the distal end of the first catheter by a second distance, and the first and second distances may be substantially equal. The loop that may be formed may have an open position that is substantially circular in shape. The lumen system may be a single lumen that may be tapered. The lumen system may include a first lumen and a second lumen, and the wire may be configured to be placed within the first lumen and extend beyond either end of the first catheter. The first catheter may be include at least two segments connected together. The retrieval device may also include, but is not limited to, a handle connected to the wire. The handle may be manipulated to cause the portion of the wire to pass through the opening system and form the loop capable of grasping foreign bodies within the patient. The retrieval device may also include, but is not limited to, a reinforcing loop material connected to the wire such that when the proximal end of the wire is manipulated to form the loop, at least a portion of the loop is adjacent to the reinforcing loop material. The reinforcing loop material may be made from TEFLON, NYLON or PTFE. The reinforcing loop material may be made from stainless steel. The reinforcing loop material may be made from nitinol. The reinforcing loop material may be made from tungsten or platinum. The retrieval device may also include, but is not limited to, a reinforcing pusher material connected to the wire proximate the proximal end of the wire. The reinforcing pusher material may be made from nitinol or stainless steel, for example. The reinforcing pusher material may be a second catheter, and the second catheter may be manipulated to cause the portion of the wire to pass through the opening system and form the loop capable of grasping foreign bodies within the patient. The retrieval device may also include, but is not limited to, a first hemostasis valve connected to the distal end of the first catheter, and a second hemostasis valve connected to the distal end of the second catheter. The retrieval may also include, but is not limited to, a side-arm adapter connected to the distal end of the first catheter. The retrieval device may also include, but is not limited to, a locking device connected to the side-arm adapter. The retrieval device may also include, but is not limited to, a hemostasis valve connected to the locking device.

In another respect, the invention is a retrieval device that includes, but is not limited to, a first catheter that has a distal end, a proximal end, a lumen system configured to accept at least one wire such that the one wire may extend beyond either end of the first catheter, and an opening system through which a loop may be formed; a first wire configured to be placed within the lumen system and extend beyond either end of the first catheter; and a second wire that has a distal end and a proximal end. The distal end of the second wire is attached to the first catheter. The proximal end of the second wire may be manipulated to cause a portion of the second wire to pass through the opening system and form a loop capable of grasping foreign bodies within a patient.

The opening system may include two openings oriented substantially equidistant from the distal end of the first catheter. The loop that may be formed may have an open position that is substantially circular in shape. The lumen system may be a single lumen. The lumen system may include a first lumen and a second lumen, the first wire may be configured to be placed within the first lumen and extend beyond either end of the first catheter, and the second wire may be placed within the second lumen. The first catheter may be tapered. The first catheter may include at least two segments connected together. The second wire may be tapered. The retrieval device may also include, but is not limited to, a handle connected to the second wire, and the handle may be manipulated to cause the portion of the second wire to pass through the opening system and form the loop capable of grasping foreign bodies within the patient. The retrieval device may also include, but is not limited to, a reinforcing loop material connected to the second wire such that when the proximal end of the second wire is manipulated to form the loop, at least a portion of the loop is adjacent to the reinforcing loop material. The retrieval device may also include, but is not limited to, a reinforcing pusher material connected to the second wire proximate the proximal end of the second wire. The reinforcing pusher material may be a second catheter configured to accept the first wire, and the second catheter may be manipulated to cause the portion of the second wire to pass through the opening system and form the loop capable of grasping foreign bodies within the patient. The retrieval device may also include, but is not limited to, a first hemostasis valve connected to the distal end of the first catheter, and a second hemostasis valve connected to the distal end of the second catheter. The retrieval device may also include, but is not limited to, a side-arm adapter connected to the distal end of the first catheter. The retrieval device may also include, but is not limited to, a locking device connected to the side-arm adapter. The retrieval device may also include, but is not limited to, a hemostasis valve connected to the locking device.

In another respect, the invention is a method for retrieving a foreign body from a patient that includes, but is not limited to, inserting a guidewire into the patient; maneuvering the guidewire to an appropriate location within the patient; advancing a first catheter, which has a distal end, a proximal end, an opening system through which a loop may be formed, and a wire attached thereto that is capable of forming a loop, over the guidewire; manipulating the wire to capture the foreign body with the loop; and withdrawing the first catheter and foreign body to retrieve the foreign body from the patient.

The opening system may include first and second openings. The first opening may be spaced from the distal end of the first catheter by a first distance. The second opening may be spaced from the distal end of the first catheter by a second distance. The first and second distances may be substantially equal. The loop that may be formed may have an open position that is substantially circular in shape. The first catheter may include at least two segments connected together. The method may also include, but is not limited to, a reinforcing loop material connected to the wire such that when the wire is manipulated to form the loop, at least a portion of the loop is adjacent to the reinforcing loop material.

BRIEF DESCRIPTION OF THE DRAWINGS

The following drawings form part of the present specification and are included to further demonstrate certain aspects of the present retrieval device. The present retrieval device may be better understood by reference to one or more of these drawings in combination with the description of illustrative embodiments presented herein.

FIG. 1 is a perspective view of one embodiment of the present retrieval device.

FIG. 2 is a front, cross-sectional view of one embodiment of the catheter of the present retrieval device.

FIG. 3 is a top view of another embodiment of the catheter of the present retrieval device.

FIG. 13 is a partial perspective view of one embodiment of the present retrieval device in which both a reinforcing loop material and a reinforcing pusher material are attached to the wire forming the loop.

FIG. 14 is a is a partial perspective view of another embodiment of the present retrieval device in which only a reinforcing pusher material is attached to the wire forming the loop.

FIG. 16 is a partial perspective view showing one embodiment of the present retrieval device in the process of retrieving a woven stent.

FIG. 18 is a front, cross-sectional view of a third embodiment of the catheter of the present retrieval device.

DESCRIPTION OF ILLUSTRATIVE EMBODIMENTS

Figure 4:
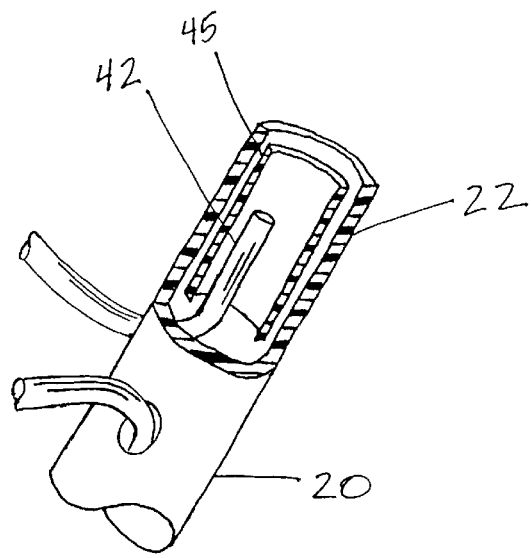
FIG. 4 is a perspective view of a portion proximate the distal end of one embodiment of the present retrieval device, which shows one manner in which the wire that forms the loop of the present retrieval device may be connected to the catheter.

Snares or retrieval devices for retrieving foreign bodies such as fragmented catheters, guidewires or pacemaker leads; or stents, filters or occlusive devices such as embolization coils should be configured to be easily and safely maneuvered through a patient's vasculature or other luminal organs. Further, the loop for use in grasping the foreign bodies should occupy as little space as possible within the vasculature or luminal organ so as to reduce to a minimum the potential for trauma of any kind as a result of its use. Similarly, the device used to transport the loop should also occupy as little space in the vasculature or luminal organ for the same reason. Additionally, the loop should be configured so as to be continuously adjustable, and capable of grasping foreign bodies of virtually all sizes such that only one or two appropriately-sized retrieval devices will adequately address a foreign body of any possible size.

Advantageously, the present retrieval devices achieve these desirable traits and overcome the problems with previous snares, such as a lack of guidewire compatibility coupled with an easily and reliably manipulable loop for grasping the target foreign body. Additionally, the present loops are continuously adjustable and, as a result, in contrast to the Amplatz snares, only one or two appropriately-sized retrieval devices according to the present disclosure need be kept on hand in order to safely and efficiently retrieve virtually any-sized foreign body resting within the vasculature or luminal organ of a patient. In further contrast to the Amplatz snare, both the catheter and the loop of the present retrieval devices are designed to occupy as little space within the vasculature or luminal organs of the patient as possible. Moreover, if a guidewire is not utilized with one of the present retrieval devices, given that one end of the wire forming the loop is attached to the catheter such that the catheter need only be large enough to accommodate a single wire segment, the size of the catheters of the present retrieval devices may be as small as possible and, accordingly, so may the access sites for the interventions utilizing the present retrieval devices. Advantageously, the possibility that the intervention may be performed on an out-patient basis may therefore be maximized.

Turning first to FIG. 1, there is shown a retrieval device 10, which includes catheter 20, guidewire 30 and wire 40. A portion of wire 40 is in the form of loop 50, discussed below in greater detail. Catheter 20 has distal end 22 and proximal end 24. Catheter 20 also has lumen system 26, as illustrated in FIG. 2. As used herein, a "catheter" is any hollow tube or cover that may be placed around objects such as wires, including guidewires, and which may enclose such object(s) and prevent contact between the object(s) and the vessel or structure into which the catheter is placed. A "catheter," as used herein, may include materials embedded within the catheter to facilitate directional control of the catheter, such as a metal braid.

In one embodiment, lumen system 26 may be a single lumen, as illustrated in FIG. 2. Both guidewire 30 and wire 40 may be housed and operate within the single lumen, as illustrated in FIG. 1. In another embodiment, shown in FIG. 3, lumen system 26 may include two lumens, one of which may be occupied by guidewire 30, and the other of which may house wire 40. Further, one of skill in the art will understand, with the benefit of this disclosure, that should more than two lumens prove useful for an application of the retrieval device 10, lumen system 26 of catheter 20 may be configured accordingly.

As shown in FIG. 1, wire 40 has distal end 42, which is hidden by catheter 20, and proximal end 44. Distal end 42 of wire 40 may be attached to catheter 20 in any suitable location using any suitable means. For example, distal end 42 may be attached to catheter 20 proximate distal end 22 of catheter 20. In this regard, distal end 42 of wire 40 may be attached to either the outside or the inside (i.e., within lumen system 26) of catheter 20 proximate distal end 22 of catheter 20. Further, distal end 42 of wire 40 may be attached to catheter 20 either closer to distal end 22 than is the hole or opening (each discussed in greater detail below) through which it is threaded, or farther from distal end 22 than is that hole or opening.

Distal end 42 may be attached to catheter 20 using any of a number of suitable means. For example, when catheter 20 is made from a metal (discussed below), such as nitinol, distal end 42 may be attached directly to catheter 20 by soldering, welding of any suitable style, an appropriate adhesive, or the like. When catheter 20 is made from a polymer (discussed below), such as TEFLON, NYLON, or the like, distal end 42 may be attached directly to catheter 20 by an appropriate adhesive, for example. It will be understood to those of skill in the art, with the benefit of this disclosure, that the amount of wire 40 that may be attached to catheter 20 may vary depending upon the application to which the retrieval device will likely be put.

In one embodiment, as shown in FIG. 4, distal end 42 of wire 40 is attached to ring 45, which is, in turn, secured to catheter 20. Ring 45 may be made from any suitable material to which wire 40 may be attached, such as stainless steel, nitinol, platinum, iridium, tungsten, or the like. Accordingly, distal end 42 may be attached to ring 45 using any suitable means, such as soldering, or welding of any suitable style, an appropriate adhesive, or the like. Further, any appropriate amount of wire 40 may be attached to ring 45. That is, wire 40 may be wound in one or more coils (distal end 42 may be among them), which may be soldered or welded, for example, to ring 45. Further still, ring 45 may be hollow, and distal end 42 may be positioned at the end of a series of coils of wire 40 within ring 45. The portion of wire 40 that is attached to ring 45 may be advantageously tapered so as to occupy less space on the outside of or within catheter 20. Ring 45 may be attached to catheter 20 using any suitable means, such as by using any suitable adhesive (e.g., glue), by creating ring 45 and catheter 20 from the same material and molding ring 45, through a friction fit, or the like.

By attaching distal end 42 of wire 40 to catheter 20, wire 40 may be manipulated in order to open and close loop 50 (described below in greater detail) with only one hand. Thus, the present retrieval devices overcome the problem noted in the Amplatz patent of needing two hands to manipulate the two ends of a wire used to form a loop. In contrast to the present retrieval devices, the Amplatz snare overcomes this problem by virtue of the bonded segments of the wire that forms the loop thereof. However, the Amplatz snare suffers from the shortcomings described above (such as the limited usefulness of a given Amplatz snare size), which stem from the bonded segments and corresponding fixed nature of the Amplatz loop. The present retrieval devices do not suffer from these shortcomings because, as a result of attaching distal end 42 to catheter 20, loop 50 is continuously adjustable. Moreover, because of the continuous adjustability of loop 50, loop 50 occupies as little space within the vasculature or luminal organ of the patient as possible during the manipulation and operation of the retrieval device. And unlike the Amplatz snares, it is feasible for an operator to retain only one or two of the present retrieval devices in order to accommodate the retrieval of virtually any-sized foreign body.

Because wire 40 of the present retrieval devices may be attached to catheter 20 so that no two portions of wire 40 overlap each other (i.e., distal end 42 of wire 40 may be attached to catheter 20 nearer distal end 22 than is the hole or opening through which it is threaded, as illustrated in FIG. 4), and because the present retrieval devices are guidewire compatible, the present retrieval devices afford operators certain advantages not available with the Amplatz, Welter and Australian snares.

For example, the Welter snare is simply not guidewire compatible. And although the Welter patent teaches the use of a stainless steel wire braid to facilitate directional control of the member of the Welter snare, when an operator utilizes guidewire 30 with the one of the present retrieval devices, it may be possible for him/her to guide the present retrieval device to the target foreign body more easily from a given location than it would be for him/her to guide the Welter snare to the target foreign body from the same location. This is true considering that guidewires are more easily maneuvered than are braided catheters. For example, guidewire 30 may be provided with a flexible angled tip.

Another advantage of using one of the present retrieval devices to retrieve a foreign body from a location that is inaccessible without a guidewire is that fewer steps may be taken to achieve the desired result with one of the present retrieval devices than with either the Welter or Amplatz snares. For example, in this situation, using any of the three devices just mentioned, a guidewire is directed to the target location. In the case of the Welter snare, a catheter sized to accommodate the Welter snare is then advanced over the guidewire. Once this catheter is suitably positioned, the guidewire is withdrawn. Then, the Welter snare is placed within the catheter and advanced to the target location. In contrast, using the present retrieval device two of the aforementioned steps—the step of withdrawing the guidewire and the step of advancing the Welter snare—are eliminated. Once guidewire 30 has been appropriately positioned, catheter 20 may be advanced over guidewire 30 to the target area, and the retrieval process may continue.

In the case of the Amplatz snare, once the guidewire is in position, a catheter configured to house the folded wire with the loop and bonded segments of the Amplatz snare is advanced over the guidewire to the target location. The guidewire is then withdrawn and replaced with the folded wire. In contrast, using the present retrieval device in the manner described above, the aforementioned step of withdrawing the guidewire is eliminated.

By eliminating various steps taken using the Amplatz and Welter snares, the retrieval of foreign bodies using the present retrieval devices will take less time than a comparable retrieval using the Amplatz or Welter snares. This time savings translates into a reduction of the potential for any complications, and thus benefits the patient. Further, as less time of the operator is required, he/she benefits as well. These time savings benefits are especially advantageous to all involved (i.e., patient, operator and assisting personnel) because it reduces radiation-exposure time, the effects of which are cumulative. Fluoroscopic X-ray guidance is normally the means by which the manipulation of retrieval devices is monitored. As a result, in order to protect him/herself, an operator may choose to perform a foreign body retrieval while wearing heavy lead protection of some kind. However, the operator will still likely be exposed to scattered radiation despite such a precaution. Therefore, since use of the present retrieval devices will likely reduce the time required to perform the retrieval in comparison to the use of either the Amplatz or Welter snares, the operator will be able to spend less time wearing physically-draining lead protection, and all individuals involved in the intervention—from patient to assistant—will be exposed to less radiation.

A further advantage afforded by the present retrieval devices utilizing guidewire 30 is that guidewire access to the target location may be continuously maintained as the operator attempts to capture the foreign body with loop 50. Continuous guidewire access is particularly important when the foreign body is in a delicate place, access to which may require a lengthy series of manipulations. Loss of guidewire access to an adjacent location—for example, in the event that the operator of either an Amplatz or Welter snare dislodges the foreign body and causes it to migrate while attempting to grasp it—could render the lengthy manipulations useless because the manipulations would have to be repeated. Furthermore, it may not even be possible to regain access to the target location because of an intervening vessel spasm, preexisting endothelial damage, or the like.

Furthermore, were the catheter of the Amplatz snare modified to be guidewire compatible, it would need to accommodate a guidewire and both segments of the wire forming the loop of the Amplatz snare since both segments are bonded together. In contrast, in embodiments of the present retrieval devices in which wire 40 is utilized without reinforcing loop material 90 (discussed below) or reinforcing pusher material 60 (discussed below) attached thereto, catheter 20 of the present retrieval devices needs only accommodate guidewire 30 (if it is used) and a single segment of wire 40 since distal end 42 of wire 40 is attached to catheter 20. Thus, catheter 20 of the present retrieval devices would take up comparatively less space in a patient's vessel or luminal organ than would either an Amplatz snare modified to accommodate a guidewire, or the Australian snare, the catheter of which must also be sized to accommodate the folded nylon line and a guidewire. Advantageously, therefore, the present retrieval devices are less likely to obstruct the flow of any passing fluids, and the risk of complications resulting from any such obstruction may be reduced.

Another benefit of the present retrieval devices is that when guidewire 30 is not utilized, the outer diameter of catheter 20 may be reduced to a size such as 2-F since lumen system 26 need only accommodate wire 40, or wire 40 attached to either or both of reinforcing pusher material 60 (discussed below) and reinforcing loop material 90 (discussed below).

Figure 5A:
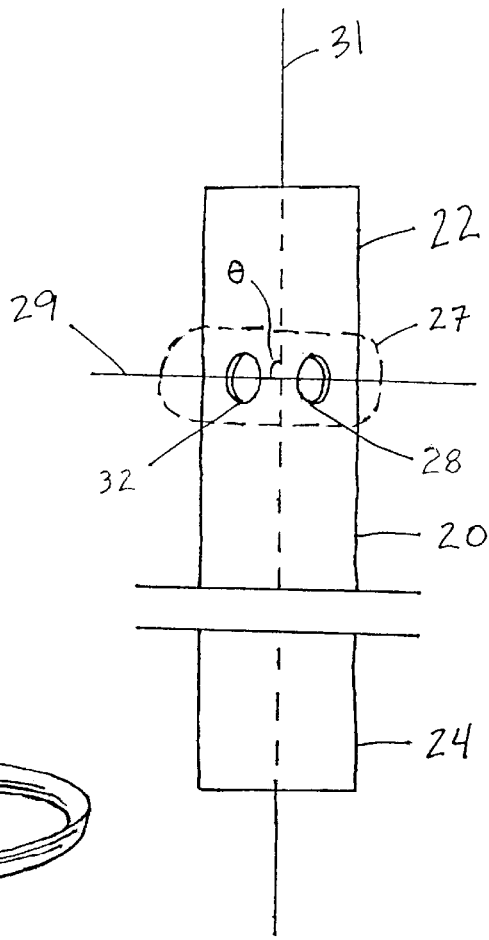
FIG. 5A is a front view of the catheter of the present retrieval device, which shows one embodiment of the opening system in the catheter.

FIG. 5A depicts opening system 27, through which loop 50 may be formed. In the embodiment of opening system 27 depicted in FIG. 5A, opening system 27 includes first opening 28 and second opening 32, both of which are provided for in catheter 20 proximate distal end 22. First opening 28 and second opening 32 are positioned substantially equidistant from distal end 22 of catheter 20. By "substantially equidistant," it is meant that the distance between distal end 22 and first opening 28 along a line that is parallel to axis 31 and the distance between distal end 22 and second opening 32 along a line that is parallel to axis 31 may be equal, or the difference in those distances may be such that the line 29 extending through the openings may be oriented at an angle θ of no greater than about 10 degrees with respect to axis 31.

While first opening 28 and second opening 32 are located substantially equidistant from distal end 22 of catheter 20 in FIG. 5A, the openings may both be positioned on opposite sides of catheter 20 (not shown) or on the same half of catheter 20 (shown). Further, the portion of wire 40 that may form loop 50 upon manipulation of proximal end 44 may occupy either the greatest distance (see FIG. 6B, here the loop is in a closed position) or the shortest distance (see FIG. 6A, here the loop is in an open position) between openings 28 and 32 along the circumference of catheter 20. Accordingly, when open or closed, loop 50 will be understood to not encircle or be wrapped around catheter 20, in contrast to the relationship of the stainless steel helical snare loop to the member of the Welter snare. Therefore, not only may wire 40 advantageously occupy a minimal amount of space exterior to catheter 20 during positioning of retrieval device 10 within a patient, but, when open, loop 50 advantageously occupies less space exterior to catheter 20 for a given radial distance from axis 31 running through lumen system 26 of catheter 20 than does the helical snare loop of Welter's snare.

The holes may be positioned at any suitable distances from distal end 22 of catheter 20. For the larger retrieval devices (defined below), the distances from distal end 22 of both first opening 28 and second opening 32 may be between about 0.5 cm and about 1.0 cm. For the smaller retrieval devices (defined below), the distances from distal end 22 of both first opening 28 and second opening 32 may be about 0.5 cm. The diameters of the holes may be slightly larger than the chosen diameter of wire 40. For example, if the diameter of reinforcing loop material 90 (which may surround wire 40 and is discussed below) is about 0.015" to about 0.018," the holes may have diameters of about 0.020" to about 0.025." As used herein, " represents inches. Thus, 0.015" is 0.015 inches.

Further, the angle of the holes with respect to axis 31 may also be adjusted. In this regard, first opening 28 and second opening 32 may each be oriented at an angle of about 90° with respect to axis 31. This angle may be adjusted to affect the angle at which a plane passing through loop 50 may be oriented.

Figure 5B:
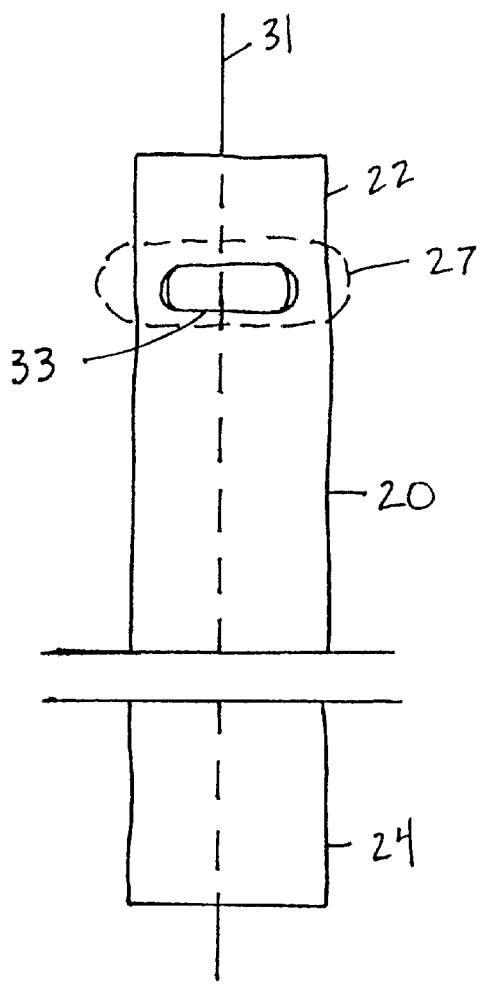
FIG. 5B is a front view of the catheter of the present retrieval device, which shows another embodiment of the opening system in the catheter.

Turning to FIG. 5B, wide opening 33, another embodiment of opening system 27, is depicted. As shown, wide opening 33 may be provided in the shape of a slot, or any other suitable shape, such as that of an hourglass or a dumbbell. Like holes 28 and 32, wide opening 33 may be positioned in catheter 20 at any suitable distance from distal end 22. Examples of such distances are described above. Also, the angle of wide opening 33 may be adjusted as described above to affect the angle at which a plane passing through loop 50 may be oriented with respect to axis 31.

By orienting first opening 28 and second opening 32 substantially equidistant from distal end 22 of catheter 20, or by orienting wide opening 33 in a way that a plane passing through loop 50 will be substantially perpendicular to axis 31, loop 50 occupies the least amount of space within the patient as possible. Specifically, the longitudinal space (i.e., the space along the length of catheter 20) occupied by loop 50 is merely the thickness of wire 40. In contrast, the wire forming the stainless steel helical snare loop of the Welter snare occupies space along the length of the member between the longitudinally spaced apart ports. Furthermore, because the stainless steel wire of the Welter snare wraps around the member, the stainless steel helical snare loop also occupies space around the circumference of the member even in its "closed" position. In contrast, loop 50 occupies space only between openings 28 and 32, for example, in its closed position.

Another benefit resulting from the orientation of first opening 28 and second opening 32, or wide opening 33, is that no space distal of catheter 20 need exist within the patient in order to safely position loop 50 around the target foreign body when approaching the foreign body from a position distal of the foreign body. This is in contrast to the fixed loop of the Amplatz snare, which must be longitudinally extended (i.e., extended along the axis of the catheter of the Amplatz snare) beyond the end of the catheter in which it is housed before it can return to its unconstrained position. Thus, as a result of the configuration of loop 50, the present retrieval device may be used in locations such as branches or bifurcations to retrieve foreign bodies from a distal approach, which could not be feasibly accessed by the Amplatz snare using such an approach.

Figure 7:
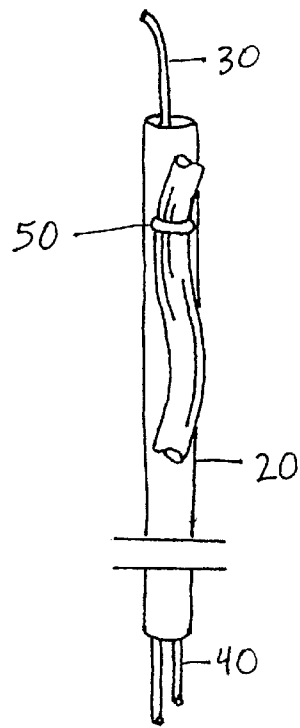
FIG. 7 is a perspective view of one embodiment of the present retrieval device, which shows a foreign body secured between the catheter and the loop.

Yet another benefit of the orientation of first opening 28 and second opening 32, or wide opening 33, of catheter 20 will be apparent in contrast to the configuration of the fixed loop of the Amplatz snare. Specifically, when the target foreign body is either straight or slightly bent, it will be oriented transversely to the catheter of the Amplatz snare when the same is used to retrieve it. As a result, the wall of the vessel or structure from which it is removed, as well as the access site, may be traumatized if any portion of the vessel or structure is smaller in diameter than the length of the laterally-oriented foreign body. Similarly, negotiating tortuous passageways may be difficult during removal, and the laterally-oriented foreign body may become caught or wedged in a passageway and require surgical removal. In contrast, these same foreign bodies may be secured next to catheter 20 with loop 50 in a longitudinally-oriented position, as illustrated in FIG. 7. As a result, the potential for traumatizing the vessel or structure of the patient is reduced to a minimum, and tortuous passageways may be more easily negotiated during removal.

Figure 6A:
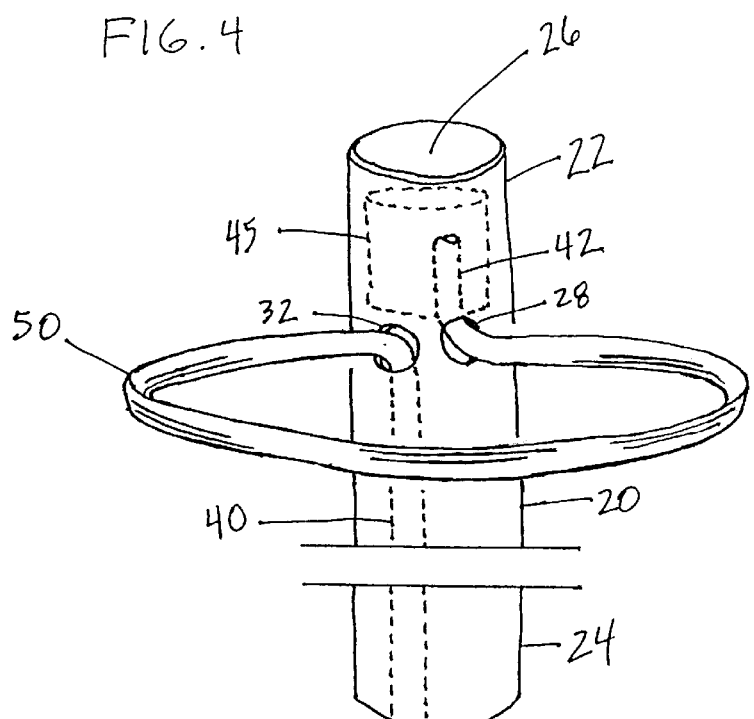
FIG. 6A is a perspective view of one embodiment of the present retrieval device, which shows the loop in an open position.
Figure 6B:
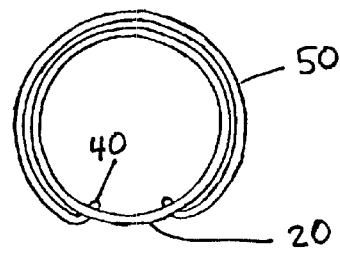
FIG. 6B is a top view showing the portion of the wire forming the loop of one embodiment of the present retrieval device occupying the greatest distance along the circumference of the catheter between the openings therein.
Figure 12:
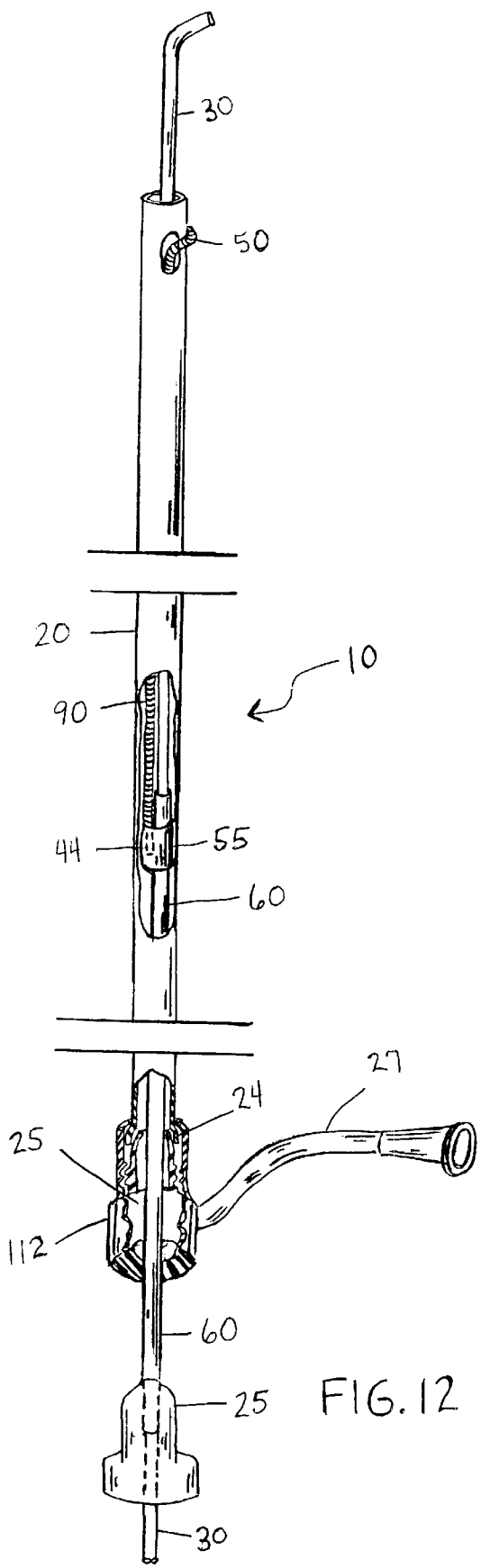
FIG. 12 is a perspective view of one embodiment of the present retrieval device, which shows hemostasis valves connected to both the catheter and the reinforcing pusher material.

As illustrated in FIG. 6A, wire 40 is positioned such that distal end 42 is attached to catheter 20 within lumen system 26 by way of ring 45 proximate first opening 28 and distal end 22, while proximal end 44 of wire 40 extends out through first opening 28, over to second opening 32, back into lumen system 26 through second opening 32, and through lumen system 26 beyond proximal end 24 of catheter 20. The portion of wire 40 positioned external of catheter 20 between first opening 28 and second opening 32 is loop 50. As shown in FIG. 6A, loop 50 is in an open position. As shown in FIGS. 7 and 12, loop 50 is in a closed position. The portion of wire 40 that forms loop 50 may be scuffed or otherwise treated in a manner that will serve to increase the friction between it and the target foreign body, in order to increase the ability of the operator to securely grasp foreign bodies with loop 50 (FIG. 7). For example, notches may be created in wire 40, or wire 40 may be deformed using any suitable means, such as by stamping a desired pattern into the wire.

Catheter 20 may be made from any suitably flexible and biocompatible material. For example, catheter 20 may be made from TEFLON. Such catheters are commercially available from Cook, Inc. (Bloomington, Ind.). Catheter 20 may also be made from NYLON. Such catheters are also commercially available from Cook, Inc. (Bloomington, Ind.). It will be understood to those of skill in the art, with the benefit of this disclosure, that material that is less flexible or firmer than either TEFLON or NYLON may also be used to form catheter 20. For example, catheter 20 may be made from metal tubing, such as nitinol microtubing, which is commercially available from Shape Memory Applications (Santa Clara, Calif.).

Depending upon whether retrieval device 10 is to be utilized with guidewire 30, the outer diameter of catheter 20 may range from 2 French (2-F) to 6-F. Accordingly, the outer diameter of catheter 20 may, for example, be 2-F, 3-F, 4-F, 5-F or 6-F. It will be understood to those of skill in the art, with the benefit of this disclosure, that catheter 20 may be configured to be either smaller in outer diameter than 2-F, such as 1.5-F, or larger in diameter than 6-F, such as 7-F, if the application requires it. The length of catheter 20 may vary according to the given application. The inventors have found that a length of about 100 cm may be useful in most applications. For use in small-vessel applications, such as neuro-interventions, the length of catheter 20 may be about 150 cm.

The inner diameter of catheter 20 may be chosen such that catheter 20 is capable of accommodating guidewire 30 and wire 40, or just wire 40. In this regard, guidewire 30 may range in size from about 0.012" to about 0.035" (which includes sizes such as 0.014", 0.016", 0.018", 0.025" and 0.035"). In one embodiment, guidewire 30 may be a 0.018" ULTRA SELECT nitinol guidewire with a flexible angled tip (commercially available from Microvena Corporation of White Bear Lake, Minn.). Examples of sizes of wire 40 are discussed below. The inventors have found that 0.010" to 0.052" is one range of acceptable inner diameters for those catheters 20 ranging from 2-F, to 6-F in outer diameter. It will be understood to those of skill in the art, with the benefit of this disclosure, that catheter 20 need not be circular in shape—either inside or out—and may possess any suitable exterior or interior shape (such as that of an ellipse) of any size comparable to those described herein.

Wire 40 may be formed from any suitably rigid yet elastic material that is suitably biocompatible. As used herein, "wire" will mean a strand formed of any such material, such as NiTi alloys like nitinol, or other materials possessing good shape memory characteristics. In this regard, other alloys that may be used include FePt, FePd, and FeNiCoTi. These alloys may be heat treated to exhibit thermoelastic martensitic transformation and, therefore, good shape memory. Other alloys such as FeNiC, FeMnSi, and FeMnSiCrNi do not possess long-range order and undergo non-thermoelastic transformation, yet exhibit good shape memory, and, thus, may also be used. Additionally, some iron-based alloys may also be used. Nitinol wires of the type that may be used successfully as wire 40 include those that are commercially available from Shape Memory Applications (Santa Clara, Calif.). Among these are nitinol wires possessing about 55 to 56% Nickel, and about 45 to 44% Titanium.

Advantageously, shape memory metals such as nitinol may be programmed with either thermal shape memory or superelastic shape memory. To program a nitinol wire with superelasticity, the wire should be restrained on a template in the desired shape (i.e., with the final size of loop 50) and annealed for 5 to 15 minutes at 500° C. To program a nitinol wire with thermal shape memory, the wire should be restrained in the same fashion and annealed for at least 60 minutes, possibly as much as 90 to 120 minutes, at 500° C. Both the superelastic and the thermal shape memory properties may be achieved at higher temperatures (up to 800° C.) if the duration of the annealing is reduced accordingly.

As a result of using materials such as nitinol for wire 40, loop 50 formed therefrom may not only be elastic and easily manipulable but also suitably rigid, in contrast to the nylon loop of the Australian snare described above. Accordingly, it is unlikely that the orientation of loop 50 would be disturbed by either a brush with the target foreign body or the vessel or structure within which it is located such that the orientation of loop 50 could not be easily regained upon manipulation of wire 40. In contrast, given the limpness of the nylon fishing line used to form the loop of the Australian snare, a disturbance to the same could prevent the operator from quickly and reliably re-achieving the proper orientation of that loop.

Figure 9:
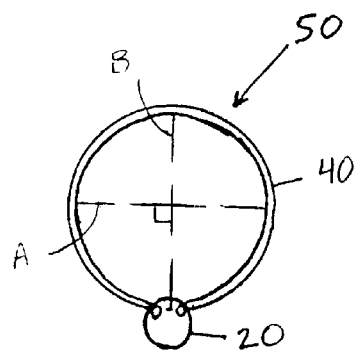
FIG. 9 is a top view of another embodiment of the present retrieval device.
Figure 8:
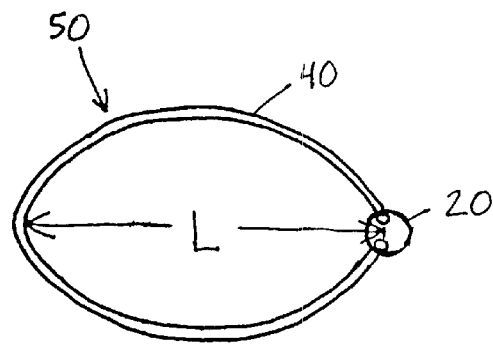
FIG. 8 is a top view of one embodiment of the present retrieval device.
Figure 10:
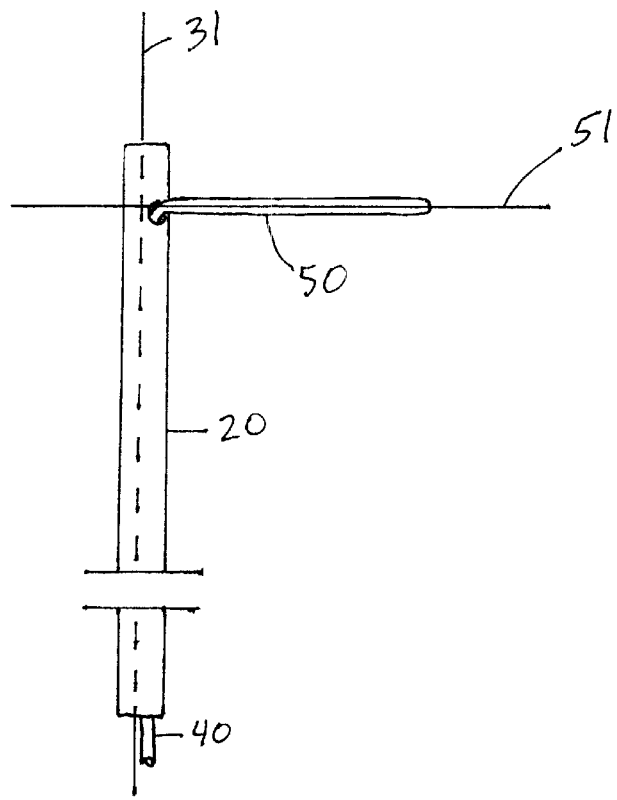
FIG. 10 is a front view of one embodiment of the present retrieval device in which the loop resides in a plane that is substantially perpendicular to an axis running through the catheter.

When programming wire 40 with either superelasticity or thermal shape memory, wire 40 may be programmed such that loop 50 has any suitable shape, such as a slightly elliptical shape as depicted in FIG. 8, or a circular shape as depicted in FIG. 9. In this regard, loop 50 may also have a shape that is only substantially circular, meaning that axes A and B, illustrated as being perpendicular to each other and crossing each other at the center of loop 50, may have lengths that differ by, for example, up to 10 percent. Loop 50 may be programmed such that it falls within a plane that is oriented substantially perpendicular to axis 31, as illustrated in FIG. 10. This spatial arrangement between the plane containing loop 50 and axis 31 of catheter 20 may be achieved as soon as loop 50 achieves a diameter (when in a substantially circular configuration) of about 6 to about 12 percent of its total diameter. Similarly, when loop 50 is some other shape, like the elliptical shape depicted in FIG. 8, this spatial arrangement between the plane containing loop 50 and axis 31 of catheter 20 may be achieved as soon as loop 50 extends to about 6 to about 12 percent of the total distance of the length L, which is the distance measured when loop 50 is in an open position (FIG. 8). In other words, as loop 50 is being opened through manipulation of wire 40, once loop 50 is at least about 6 to about 12 percent of the foregoing dimensions, the portion of loop 50 that is exterior to catheter 20 at any given time thereafter will be in a plane that is substantially perpendicular to axis 31 of catheter 20.

It will be understood to those of skill in the art, with the benefit of this disclosure, that loop 50 may be programmed with superelasticity or thermal shape memory so as to exist in a plane that is oriented at any suitable angle with respect to axis 31. However, as shown in FIG. 10, in virtually all applications, programming wire 40 with superelasticity so that loop 50 lies in a plane (like plane 51) that is substantially perpendicular to axis 31 will provide the most useful orientation of loop 50 for quickly and efficiently capturing foreign bodies.

Figure 11:
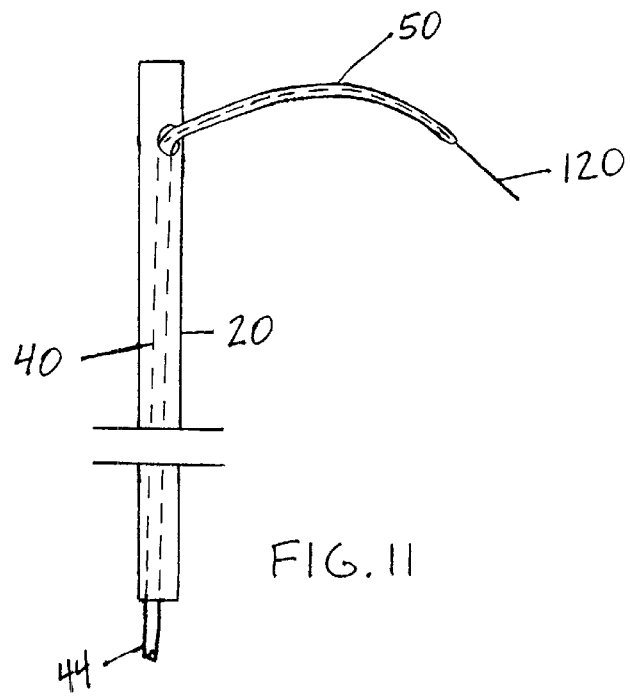
FIG. 11 is a front view of another embodiment of the present retrieval device in which a longitudinal axis that is curved passes through the loop.

As shown in FIG. 11, loop 50 may be provided with a longitudinal axis 120 that is curved. Although FIG. 11 shows longitudinal axis 120 curved such that loop 50 points downwardly toward proximal end 44 of wire 40, it will be understood to those of skill in the art, with the benefit of this disclosure, that wire 40 may be programmed with superelasticity or thermal shape memory such that loop 50 is curved in the opposite direction.

Although retrieval device 10 may be configured so as to be useful in all the vessels or luminal organs within the body of a patient, it will be understood to those of skill in the art, with the benefit of this disclosure, that it is reasonable for a surgeon or an operator to be prepared to deal with a foreign body of virtually any size using either of two of the present retrieval devices that are configured with different sizes. In this regard, a "smaller retrieval device" may be configured for applications that are performed within a vessel or luminal organ with a diameter of less than about 1 cm (e.g., nueroradiological applications), and may be provided with wire 40 and reinforcing loop material 90 (discussed below), which may be attached to wire 40, such that the diameter or the length L (FIG. 8) of loop 50, when loop 50 is open, may be between about 2 mm and about 7 mm. A "larger retrieval device" may be used for all other applications, and may be provided with wire 40 and reinforcing loop material 90, which may be attached to wire 40, such that the diameter or the length L (FIG. 8) of loop 50, when loop 50 is open, may be between about 5 mm and about 45 mm.

The size of wire 40 may vary according to the given application. For the smaller retrieval devices, wire 40 may range in size from about 0.004" to about 0.006" (which includes 0.004", 0.005" and 0.006"), and may be made from nitinol. For the larger retrieval devices, wire 40 may range in size from about 0.007" to about 0.012" (which includes 0.007", 0.008", 0.009", 0.010", 0.011" and 0.012"), and may be made from nitinol. It will be understood to those of skill in the art, with the benefit of this disclosure, that wire 40 may be larger or smaller than the sizes encompassed within these exemplary ranges.

The smaller retrieval device should be provided with a catheter 20 possessing the smallest feasible outer diameter. Accordingly, it will be understood to those of skill in the art, with the benefit of this disclosure, that the catheter useful in the smaller retrieval device may have an outer diameter of, for example, 2-F, 3-F, or 4-F. The inner diameters of such catheters may range, for example, from 0.012" to 0.018".

Regarding the larger retrieval devices, the size of the outer diameter of catheter 20 in such devices may be, for example, 4-F, 5-F, or 6-F. Catheter 20 may be provided with lumen system 26 having a lumen capable of accepting or housing wire 40; when wire 40 is between about 0.005" and about 0.010", and to which reinforcing pusher material 90 (discussed below in greater detail) having an outer diameter of from about 0.015" to about 0.020" is attached; along with guidewire 30 having a diameter of 0.018".

Further, when used with either the smaller or larger retrieval device, catheter 20 may be formed from pieces or portions of catheters having different outer diameters. In one such embodiment, catheter 20 may be formed from pieces of catheters, which may be made from the materials described above, having different outer diameters (or differing shapes if the catheters are not round) such that distal end 22 of catheter 20 may be formed from a piece of a catheter with an outer diameter that is smaller than the outer diameter of the piece of catheter from which proximal end 24 may be formed. The different catheter pieces may be joined together using well-known techniques, such as molding, casting or the like, so as to form an integral catheter 20 having a relatively smooth transition area where the pieces come together. Similarly, the different pieces of differently-sized catheters may be arranged so as to effectively taper catheter 20, such that distal end 22 is provided on a piece of catheter that may have a smaller outer diameter than that of the piece of catheter on which proximal end 24 is provided. Catheter 20 may also be extruded or otherwise manufactured so as to be tapered externally or internally (i.e., such that it has, for example, a single lumen that is tapered).

In this regard, as used herein, a "tapered" catheter means a catheter that has either (a) an outer surface having a first cross-sectional area defined by the outer surface at a first location that differs from a second cross-sectional area defined by the outer surface at a second location, or (b) an inner surface (which defines lumen system 26 as used herein) having at least a first cross-sectional area defined by the inner surface at a first location that differs from a second cross-sectional area defined by the inner surface at a second location. The aforementioned cross-sectional areas are to be understood as having been taken at an angle that is perpendicular to a longitudinal axis of the catheter (e.g. axis 31 shown in FIG. 5A). A tapered catheter 20 that satisfies both (a) and (b) is illustrated in FIG. 18.

The size and configuration of lumen system 26 of catheter 20 may also vary according to the given application. As described above, if lumen system 26 includes only a single lumen, the inner diameter of catheter 20 (i.e., the diameter of lumen system 26) may range in size from about 0.010" to about 0.052". Catheters or pieces of catheters that are assembled to form catheter 20 may be provided with one or more lumens in which, for example, wire 40 and/or guidewire 30 may be housed. Lumen system 26 of catheter 20 of the smaller retrieval device may have a tapered lumen (i.e., a catheter satisfying portion (b) of the definition of a tapered catheter set forth above) configured to accept a guidewire 30 that is about 0.012" to about 0.014" in diameter, and a wire 40 having a diameter of about 0.004" to about 0.006" to which a reinforcing loop material 90 (discussed below and illustrated in FIGS. 12 and 13) having an outer diameter of about 0.010" to about 0.015" is attached.

It may be desirable in certain applications to increase the pushability of wire 40. In other words, it may be desirable to reduce the possibility that wire 40 may kink or buckle as loop 50 is opened. This may be accomplished by providing wire 40 with a reinforcing pusher material. As used herein, a "reinforcing pusher material" is any material that may be attached or connected to wire 40 in any fashion to increase the stiffness of any segment of wire 40. FIGS. 12 and 13 illustrate reinforcing pusher material 60. The result of attaching reinforcing pusher material 60 to wire 40 is that the operator may easily exert enough force to move wire 40 distally (push) and proximally (pull).

As shown in FIGS. 12–14, in one embodiment of retrieval device 10, reinforcing pusher material 60 may be a piece of metal tubing. In this regard, the metal tubing may be made from nitinol that possesses superelastic qualities. Such nitinol tubing is available from Shape Memory Applications (Santa Clara, Calif.) with pre-programmed superelasticity, and may possess about 55 to 56% Nickel, and about 45 to 44% Titanium. Other materials such as stainless steel tubing, or nitinol or stainless steel wire may also be used for reinforcing pusher material 60.

In one embodiment in which reinforcing pusher material 60 is made from metal tubing, the tubing may be slipped over proximal end 44 of wire 40 and attached using one of the means described below, as shown in FIG. 14. In another embodiment in which reinforcing pusher material 60 is made from metal tubing, the tubing may be placed beside some segment of wire 40 adjacent proximal end 44 thereof, as shown in FIGS. 12 and 13 (wire 40 is shown as being covered by reinforcing loop material 90, discussed below), and attached using one of the means described below. In this embodiment, the tubing may be configured to accept guidewire 30, as illustrated in FIGS. 12 and 13.

Reinforcing pusher material 60 may be attached to wire 40 using any suitable means. For example, the two may be attached via soldering or welding of any suitable style. The length along which the two may be attached may be any length suitable for achieving a reliable attachment between the two. In one embodiment, the length may be at least 1 cm or longer. One or more attachment sites may be used. Alternatively, a notch or groove (longitudinal or helical in direction, for example) may be provided in reinforcing pusher material 60; wire 40 may be placed in that notch or groove; and the two may be soldered, welded, glued, or friction fitted together. In addition, ring 55 (FIG. 12) may be placed over wire 40 and reinforcing pusher material 60 along any portion of either, including proximal end 44, to serve as the means of attaching the two together. Ring 55 may be made of any suitable material, and may be used alone or with soldering or welding.

Turning to the lengths of wire 40 and reinforcing pusher material 60, wire 40 should be at least as long as the portion of wire 40 that will extend from distal end 42 through loop 50, and should include the length of the attachment site between wire 40 and reinforcing pusher material 60, if reinforcing pusher material 60 is used. In turn, if loop 50 is open, reinforcing material 60 should extend from the point at which it is attached to wire 40 to beyond the most proximal attachment, if any, to catheter 20 (such as hemostasis valve 25 depicted in FIG. 17) by an extent sufficient to allow for manipulation of reinforcing pusher material 60 in order to form an open loop 50. If reinforcing material 60 is not used, wire 40 should be at least as long as the portion of wire 40 that will extend from distal end 42 through loop 50 to beyond the most proximal attachment, if any, to catheter 20 by an extent sufficient to allow for manipulation of proximal end 44 of wire 40 in order to form an open loop 50. Additionally, both the diameter and the length of reinforcing pusher material 60 may be chosen so as to leave the distal portion of catheter 20 reasonably floppy and flexible thereby facilitating the superselective positioning of retrieval device 10.

The pushability of wire 40 may also be increased by utilizing a tapered wire. In this regard, the distal end of wire 40, which may be made from nitinol, may have a diameter of, for example, 0.003", 0.004", 0.005", or 0.006" for the smaller retrieval device and 0.006", 0.007", 0.008", 0.009", 0.010", 0.011", or 0.012" for the larger retrieval device. The proximal end—that is, proximal end 44—of such wires may then be gradually increased in diameter to about 0.020" for use with the smaller retrieval devices and about 0.035" for use with the larger retrieval devices. The portion of wire 40 that forms loop 50 may possess a consistent diameter, or may be tapered. As used herein, a "tapered" wire or a "tapered" portion of a wire means a wire or a portion of a wire that has a first cross-sectional area defined by the outer surface of the wire or portion of the wire at a first location that differs from a second cross-sectional area defined by the outer surface of the wire or portion of the wire at a second location. The aforementioned cross-sectional areas are to be understood as having been taken at an angle that is perpendicular to a longitudinal axis running through the wire or portion of the wire.

Another manner of increasing the pushability of wire 40 may be facilitated by utilizing multiple lumens within lumen system 26 of catheter 20. Accordingly, wire 40 may be placed in one of the lumens, and another lumen may be occupied by guidewire 30, as described above.

In the embodiment of retrieval device 10 illustrated in FIG. 12, hemostasis valve 25 is connected to proximal end 24 of catheter 20, and may be used to control the flow of fluid through catheter 20. Hemostasis valve 25 may be connected to catheter 20 in any manner well known in the art, such as a traditional Luer lock mechanism (not shown). Alternatively, in the embodiment illustrated in FIG. 12, proximal end 24 may be flared and attached to the hub of hemostasis valve 25 using catheter adapter 112. As shown, catheter adapter 112 is threadably engaged with the hub of hemostasis valve 25, and secures flared proximal end 24 of catheter 20 between hemostasis valve 25 and catheter adapter 112. Catheter adapter 112 may also be configured to allow for side arm 27 to be attached to hemostasis valve 25, as illustrated. Hemostasis valve 25 serves the function of preventing fluid from escaping around the wire or reinforcing pusher material it houses. Throughout the present disclosure, the hemostasis valves that may be utilized as part of the present retrieval devices will each be designated as hemostasis valve 25, although variations in size among those utilized may be appropriate. Further, the manner of connecting the hemostasis valves herein to other devices may be achieved using any appropriate mechanisms, including those just described. Fluids such as contrast or a saline flush may be injected into the lumen system of catheter 20 through side arm 27. In another embodiment, a tightening screw mechanism (not shown), which utilizes a compressible, resilient ring that would tighten around flared proximal end 24 when the mechanism was engaged with valve 25, may be utilized instead of catheter adapter 112, and may be configured to allow for side arm 27 to be attached to hemostasis valve 25. Glue may be used to further reinforce the connection between catheter 20 and hemostasis valve 25, regardless of the means of connection utilized. Also shown in FIG. 12, reinforcing pusher material 60 may be provided with hemostasis valve 25.

As illustrated in FIGS. 12 and 13, reinforcing pusher material 60, which is a tube, has a lumen configured to accept guidewire 30. This lumen may be sized so as to accept a variety of differently-sized guidewires 30. For example, the lumen may be sized to accept a guidewire 30 having a diameter of 0.018". Although a guidewire 30 having a diameter of 0.018" may provide sufficient rigidity and excellent maneuverability in most cases for either the larger or smaller retrieval devices, the lumen of reinforcing pusher material 60 may be configured to accept smaller guidewires 30, such as those having a diameter of 0.014" in the case of the smaller retrieval devices, or larger guidewires, such as those having diameters of 0.025" in the case of the larger retrieval devices.

Also illustrated in FIGS. 12 and 13, in some embodiments of the present retrieval devices, at least a portion of the segment of wire 40 that forms loop 50 may be provided with reinforcing loop material 90. Also, as illustrated in FIG. 13, reinforcing loop material 90 may extend along a greater length of wire 40 than that which will form part or all of open loop 50. As used herein, a "reinforcing loop material" is any material that may be attached or connected to wire 40 so as to increase the stiffness of some or all of the portion of wire 40 that may form open loop 50. Depending on the material used, reinforcing loop material 90 may be (either "naturally" or after being treated in some fashion) rougher than wire 40, such that the friction between the foreign body and loop 50 may be increased relative to the friction between wire 40 and foreign body.

Reinforcing loop material 90 may be made of any suitably rigid yet elastic material that is suitably biocompatible. For example, reinforcing loop material 90 may be made of stainless steel, nitinol, TEFLON, NYLON, or PTFE. These materials may be provided in a tubular form such that they may be fitted over wire 40, provided they are sufficient flexible to allow for the formation of loop 50. Reinforcing loop material 90 may also be provided in wrapping wire form such that reinforcing loop material 90 is a hollow coil having an inner and outer diameter that may be fitted over wire 40. When reinforcing loop material 90 is provided either as a tube or a hollow coil, the inner diameter thereof is determined by the diameter of wire 40 and, in this regard, is generally only slightly greater than the diameter of wire 40. The outer diameter of reinforcing loop material 90 depends on the material that is used. In this regard, reinforcing loop material 90 with an outer diameter of 0.018" is suitable for use with larger retrieval devices, while an outer diameter of 0.012" is suitable for use with smaller retrieval devices.

In another embodiment, reinforcing loop material 90 may take the form of a wire that is manually wrapped around wire 40. Such a wire may be made from nitinol and possess 55 to 56% Nickel, and about 45 to 44% Titanium (Shape Memory Applications). Additionally, reinforcing loop material 90 may be provided with a radiopaque material such as tungsten or platinum. In this regard, reinforcing loop material 90 may be made exclusively from the highly radiopaque material, such as tungsten or platinum, or may be formed from a mixture of a highly radiopaque material and a less radiopaque material such as stainless steel or nitinol.

Reinforcing loop material 90 may be attached to wire 40 using any suitable means, such as through the use of welding of any suitable style, soldering or gluing. In this regard, both ends of reinforcing loop material 90 may be attached to wire 40, or any number of attachments sites between the ends of reinforcing loop material 90 may be created. Similarly, reinforcing loop material 90 may be attached to wire 40 along the entire length of reinforcing loop material 90, especially using glue. Prior to or after a suitable attachment has been made, if reinforcing loop material 90 is made of a suitable material, such as nitinol, it and wire 40 may be annealed together as described above. Regardless of the form of reinforcing loop material 90, once the same is attached to wire 40, when the proximal end of the wire 40 is manipulated to open or close loop 50, at least a portion of loop 50 will be understood to be adjacent to reinforcing loop material 90.

In certain applications, such as superselective positions in the pulmonary arteries, catheter 20 should have a low profile so as to maximize trackability. Accordingly, in the case of the larger retrieval devices, catheter 20 may be provided with an outer diameter of 6-F, wire 40 may be provided with a diameter of 0.009", and reinforcing loop material 90, if used, may be provided with an outer diameter of 0.018". In this same regard, in the case of the smaller retrieval devices, catheter 20 may be provided with an outer diameter of 3-F, wire 40 may be provided with a diameter of 0.005", and reinforcing loop material 90, if used, may be provided with an outer diameter of 0.012". As a result, both the smaller and retrieval devices provided with such dimensions will likely be able to easily negotiate tortuous sections of the vasculature or other luminal organs, and/or acute angles in either, following guidewire 30.

Figure 15:
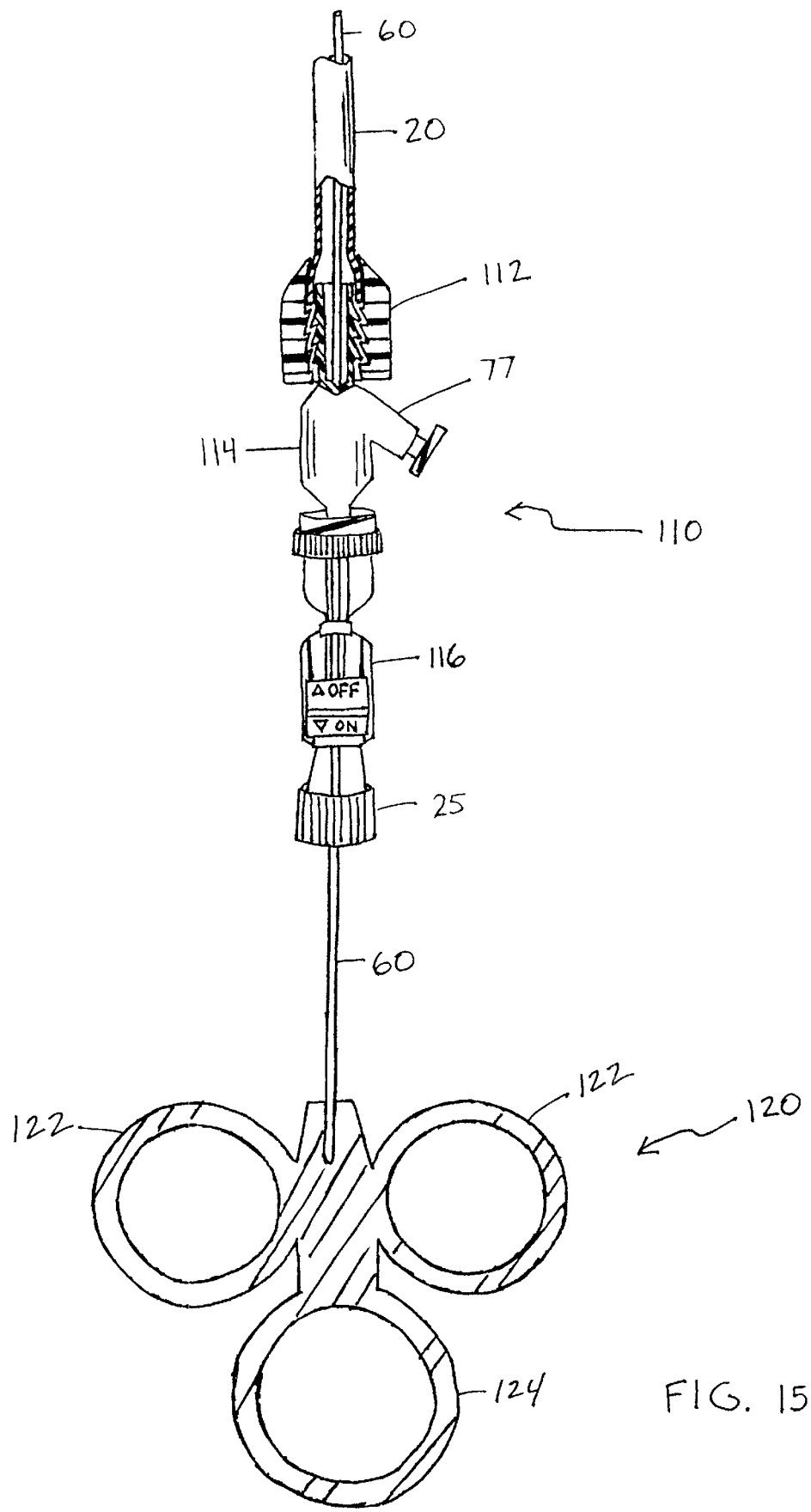
FIG. 15 is a partial perspective view of one embodiment of the present retrieval device, which shows a locking system attached to the distal end of the catheter and a handle attached to the distal end of the reinforcing pusher material.

Turning to FIG. 15, catheter 20 may be equipped with lock system 110 and handle 120. Lock system 110 may include catheter adapter 112, which is capable of connecting catheter 20 to side-arm adapter 114 in the manner described above. Guidewire 30 (not shown) may be introduced through side-arm adapter 114. In this regard, catheter 20 may also be positioned and advanced over a guidewire that is already in place, as described in greater detail below. The lumen of side-arm adapter 114 may be configured to direct a guidewire entering the adapter from the distal end thereof—such as if catheter 20 were advanced over an already-positioned guidewire 3—to arm 77. This may be achieved by a divider within the lumen of the side-arm adapter 114, or the like.

Also illustrated in FIG. 15, lock system 110 may also include locking device 116, which is shown as being connected to side-arm adapter 114, and which may be used to secure reinforcing pusher material 60 or wire 40 (not shown) relative to catheter 20. When the two are secured in this manner, neither reinforcing pusher material 60 (or wire 40) nor catheter 20 will be able to move axially relative to the other. Suitable locking devices 116 include the FloSwitch®HP (commercially available from Meditech/Boston Scientific Corp., Watertown, Mass.), a tightening screw mechanism, and a push-button mechanism, for example. Other similarly-functioning devices may also be used as locking device 116. Hemostasis valve 25 may be connected to the proximal end of locking device 116. Just as a Luer lock may be used for attaching hemostasis valve 25 to locking device 116, so may one be used as the connecting mechanism for attaching locking device 116 to side-arm adapter 114.

As shown in FIG. 15, handle 120 may be attached directly to reinforcing pusher material 60 or wire 40 (not shown). Using handle 120, an operator may push or pull wire 40 as necessary to open or close loop 50. Although not shown, it will be understood to those of skill in the art, with the benefit of this disclosure, that finger pieces 122 may be attached directly to reinforcing pusher material 60 or wire 40. Further, thumb piece 124 may be connected to lock system 110, and finger pieces 122 may be slidably moved relative to stationary thumb piece 124. Any suitable device may be attached to the proximal end of reinforcing pusher material 60 or wire 40 (not shown) for the purpose of facilitating the manipulation of either.

It will be understood to those of skill in the art, with the benefit of this disclosure, that any of the present retrieval devices 10 may be used with or without lock system 110 or handle 120.

Figure 17:
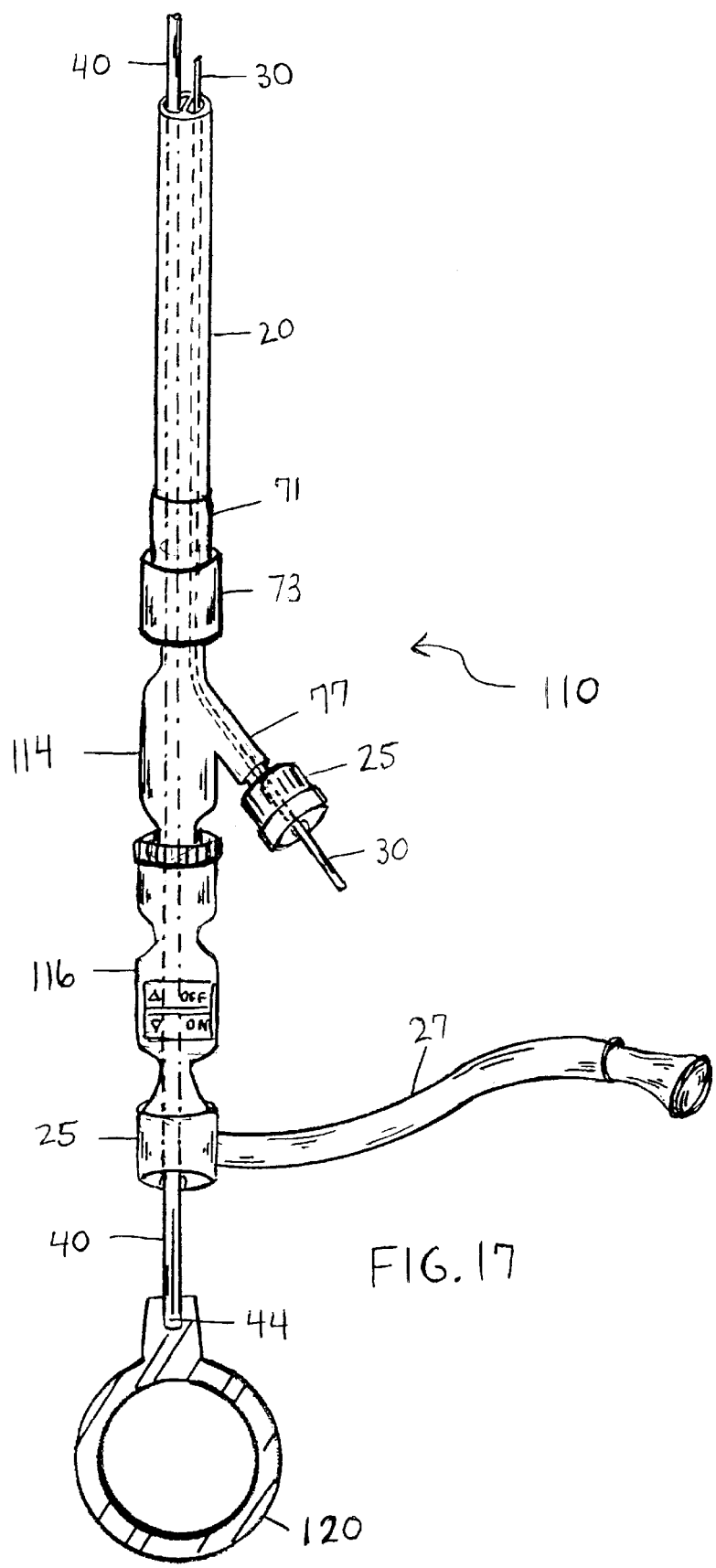
FIG. 17 is a partial perspective view of one embodiment of the present retrieval device, which shows a dual-lumen lumen system in the catheter, a locking system attached to the distal end of the catheter and a handle attached to the distal end of the wire that forms the loop.

Another embodiment of locking system 110 is depicted in FIG. 17. As shown, the lumen system of catheter 20 includes two lumens. Wire 40 is housed in one of the lumens, and guidewire 30 is housed in the other lumen. Proximal end 24 (hidden) of catheter 20 is provided with catheter hub 71, which is configured as a female Luer connection piece. Catheter hub 71 may be glued or otherwise attached to catheter 20 at proximal end 24. Catheter hub 71 may also be formed integrally with catheter 20 (not shown). As shown, catheter 20 may be attached to side-arm adapter 114 by virtue of the male Luer connection piece 73 engaging catheter hub 71. Hemostasis valve 25 may be attached to arm 77 of side-arm adapter 114, to serve at least the function of preventing blood loss around guidewire 30.

Also shown in FIG. 17, locking system 110 may include locking device 116, which may be any of the devices described above with reference to FIG. 15. Locking device 116 may be connected to side-arm adapter 114 using a Luer lock. Further, locking device 116 may be attached to hemostasis valve 25. Hemostasis valve 25 may be provided with side arm 27, through which any suitable fluid may be injected into lumen system 26, just as any suitable fluid may be injected through arm 77 upon removal of hemostasis valve 25. To better ensure that a suitable fluid may be forced through both lumens of a multi-lumen lumen system 26, the lumens may be provided with any suitable means of communication between them, such as a series of one or more openings in the partition dividing the lumens. In this regard, the partition may be porous. Care should be taken, however, to guard against configuring lumen system 26 in a way that would promote or increase the likelihood that guidewire 30 could mistakenly be directed to the wrong lumen during operation.

As illustrated in FIG. 17, handle 120, shown as being attached to wire 40 proximate proximal end 44 of wire 40, may be a single ring. In this regard, any suitable device may be attached to the proximal end of wire 40 or reinforcing pusher material 60 (not shown) for the purpose of facilitating the manipulation of either.

With further regard to FIG. 17, the lumen of side-arm adapter 114 may be configured to direct a guidewire entering the adapter from the distal end thereof—such as if catheter 20 were advanced over an already-positioned guidewire 30—to arm 77. This may be achieved by a divider within the lumen of the side-arm adapter 114, or the like. Additionally, were guidewire 30 inserted into side-arm adapter 114 through arm 77, the lumen of lumen system 26 in which wire 40 is housed may be narrowed in any suitable fashion at proximal end 24 of catheter 20 in order to better ensure that guidewire 30 advances through the other lumen of lumen system 26. This narrowing may be achieved by any suitable insert (not shown), such as an elastic ring or the like, that can be friction-fitted, glued, extruded or otherwise integrally-formed, etc., within the proximal end of the lumen so as to allow the least amount of free space to surround wire 40 (or reinforcing pusher material 60, not shown) once wire 40 is in place. By doing so, guidewire 30 is less likely to be mistakenly inserted into the lumen of lumen of lumen system 26 occupied by wire 40, should the lumen of side-arm adapter 114 not be provided with a divider or other element for properly directing guidewire 30. However, it will be understood to those of skill in the art, with the benefit of this disclosure, that careful manipulation of guidewire 30 will likely ensure the proper placement thereof even absent a divider within the lumen of side-arm adapter 114 or a narrowing insert in the appropriate lumen of lumen system 26.

The present retrieval devices may be used in a variety of applications for retrieving foreign bodies of virtually any size. In most cases, the present retrieval devices may be inserted into patients by way of a single percutaneous insertion. In this regard, the access vessel or luminal organ may be punctured through the skin with an appropriate needle. Guidewire 30 may be inserted into the body through the lumen of the needle and the needle may be removed. The guidewire may then be maneuvered through the patient until it reaches an appropriate location, such as one proximate the foreign body. Once guidewire 30 has been positioned in a suitable location, catheter 20 of the present retrieval device may be advanced over the guidewire until it is appropriately positioned as well.

If the retrieval device being utilized is provided with lock system 110 and handle 120, once the retrieval device has reached the target area—which may or may not involve further manipulations of guidewire 30 and catheter 20—loop 50 may be manipulated and the operator may attempt to grasp the foreign body with it. In doing so, locking device 116 may be temporarily unlocked, and handle 120 may be manipulated so as to open loop 50. Locking device 116 may then be re-locked. Loop 50 may then be maneuvered so as to surround the foreign body; locking device 116 may be temporarily unlocked; handle 120 may be manipulated until the foreign body is firmly connected between loop 50 and catheter 20; and locking device 116 may be re-locked. The retrieval device, along with the foreign body, may then be withdrawn and removed from the patient.

An introducer sheath may be used during the intervention if doing so is in the best interest of the patient. Introducer sheaths are normally used if the access site is expected to be used several times, which normally occurs when catheters or other devices are exchanged. Usually, the use of one of the present retrieval devices may be necessary to remedy an undesired complication that occurs during an intervention. Because such an intervention may have involved the use of an introducer sheath, the present retrieval device may also be inserted through that introducer sheath. If an initial introducer sheath does not seem suitable for safe removal of the given foreign body, the operator may exchange it for an appropriately-sized one before starting the retrieval process. One advantage of utilizing an introducer sheath is the reduction in the possibility that the foreign body may cause damage to the access site during removal.

If the present retrieval device used in an intervention is not used with guidewire 30, access to the vessel or luminal organ may be established as just described. A guidewire may then be maneuvered through the patient until it reaches the approximate location of the foreign body. An appropriately-sized catheter (i.e., a guiding catheter or the like that will fit over catheter 20) may then be advanced over the guidewire to the target location. The guidewire may be withdrawn, and catheter 20 may be advanced to the target location within the appropriately-sized catheter. The appropriately-sized catheter may then be partially withdrawn to allow the operator to manipulate the retrieval device in an unfettered manner.

It may be desirable in some cases to utilize the appropriately-sized catheter to help capture or firmly hold the foreign body. In such cases, the tip of the appropriately-sized catheter may be advanced over the retrieval device to openings 28 and 32 or wide opening 33, the point at which wire 40 exits or enters catheter 20. The rim of the end of the appropriately-sized catheter may then be used to reinforce the contact between loop 50, the foreign body, and catheter 20. If the appropriately-sized catheter plays no role in the retrieval process, it may be positioned so as to allow the free operation of the retrieval device, and may then be fixedly secured to catheter 20 using a device similar to one that may serve as locking device 116.

When loop 50 is being opened or closed through the manipulation of either wire 40 or reinforcing pusher material 60, whether or not handle 120 is utilized, it will be understood to those of skill in the art, with the benefit of this disclosure, that depending on its orientation, the target foreign body may be approached from its proximal end or its distal end. In either case, once loop 50 has been appropriately positioned around the target foreign body, loop 50 may be manipulated so that the foreign body is secured against the outside of catheter 20. In some cases, in order to best orient the foreign body longitudinally such that the axis, if any, of the foreign body is as parallel to axis 31 of catheter 20 as possible, loop 50 may be loosened and retightened one or more times. Once the target foreign body has been secured in this manner, the retrieval device and the foreign body may be withdrawn together and removed from the body. As indicated above, an access sheath may be used to minimize the potential for damage to the access site during removal.

It will be understood to those of skill in the art, with the benefit of this disclosure, that the present retrieval devices can also be surgically inserted into a patient.

The present retrieval devices may also be utilized to retrieve various stents, such as the Palmaz-Schatz stent, the Wallstent® or the Gianturco-Roubin stent. As shown in FIG. 16, to retrieve such a stent, a guidewire 130 may be placed into the lumen of the stent 132. Next, a sheath or guiding catheter 134 may be advanced over guidewire 130 until positioned proximally of stent 132. Retrieval device 10 may then be advanced within the sheath or guiding catheter until it is appropriately positioned either distally or proximally of the stent. Once loop 50 has been opened and oriented appropriately around the stent to be retrieved, guidewire 30 may be completely withdrawn, loop 50 may be closed around the stent by manipulating proximal end 44 of wire 40 (not shown) through the use of handle 120 (not shown), and retrieval device 10 and the secured stent 132 may be simultaneously withdrawn over guidewire 130 into guiding catheter 134 and out of the patient's body.

All of the present retrieval devices disclosed and claimed herein can be made and executed without undue experimentation in light of the present disclosure. While the techniques of this invention have been described in terms of specific embodiments, it will be apparent to those of skill in the art that variations may be applied to the present retrieval devices without departing from the concept, spirit and scope of the invention. For example, all the connections between the elements that may be included in locking system 110—such as side-arm adapter 114 and locking device 116 depicted in FIGS. 15 and 17—may be reinforced using glue, or any suitable adhesive.

REFERENCES

The following references, to the extent that they provide exemplary procedural or other details supplementary to those set forth herein, are specifically incorporated herein by reference.

Bett et al, "Plastic catheter embolism to the right heart a technique of non-surgical removal," *Med. J of Aust.*, 854–856, 1971.

Bloomfield, "The nonsurgical retrieval of intracardiac foreign bodies—an international survey," *Cathet. Cardiovasc. Diagn.*, 4:1–14, 1978.

Galal et al., "Problems encountered during introduction of Gianturco coils for transcatheter occlusion of the patent arterial duct," *Eur. Heart J.*, 18:625–630, 1997.

Ing and Bierman, "Percutaneous transcatheter coil occlusion of the patent ductus arteriosus aided by the nitinol snare: further observations," *Cardiovasc. Intervent. Radiol.*, 18:222–226, 1995.

Lipton et al., "Percutaneous retrieval of two Wallstent endoprostheses from the hear through a single jugular sheath," *JVIR*, 6:469–472, 1995.

Siegel and Robertson, "Percutaneous transfemoral retrieval of a free-floating Titanium Greenfield filter with an Amplatz goose neck snare," *JVIR*, 4:565–568, 1993.

What is claimed is:

1. A retrieval device comprising:
   first catheter having a distal end, a proximal end, a lumen system configured to accept at least one wire such that the at least one wire may extend beyond either end of the first catheter, and an opening system through which a loop may be formed, the opening system positioned between the distal end and the proximal end, the lumen system having an opening separate from the opening system, the opening of the lumen system configured to accept the at least one wire such that the at least one wire may extend beyond the distal end of the first catheter; and
   a wire having a distal end attached to the first catheter, and a proximal end;
   wherein the proximal end of the wire may be manipulated to cause a portion of the wire to form a loop external of the first catheter, the loop being capable of grasping foreign bodies within a patient.

2. The retrieval device of claim 1, further comprising a guidewire configured to be placed within the lumen system.

3. The retrieval device of claim 1, wherein the opening system comprises first and second openings, the first opening being spaced from the distal end of the first catheter by a first distance, the second opening being spaced from the distal end of the first catheter by a second distance, the first and second distances being substantially equal.

4. The retrieval device of claim 1, wherein the loop that may be formed has an open position that is substantially circular in shape.

5. The retrieval device of claim 1, wherein the lumen system comprises a single lumen.

6. The retrieval device of claim 1, wherein the first catheter is tapered.

7. The retrieval device of claim 1, wherein the lumen system comprises a first lumen and a second lumen, and wherein the first lumen is configured to accept at least (a) a guidewire such that the guidewire may extend beyond either end of the first catheter, and (b) a wire suited to forming the loop.

8. The retrieval device of claim 1, wherein the first catheter comprises at least two segments connected together.

9. The retrieval device of claim 1, further comprising a handle connected to the wire, and wherein the handle may be manipulated to cause the portion of the wire to pass through the opening system and form the loop capable of grasping foreign bodies within the patient.

10. The retrieval device of claim 1, further comprising a reinforcing loop material connected to the wire such that when the proximal end of the wire is manipulated to form the loop, at least a portion of the loop is adjacent to the reinforcing loop material.

11. The retrieval device of claim 10, wherein the reinforcing loop material comprises stainless steel.

12. The retrieval device of claim 10, wherein the reinforcing loop material comprises nitinol.

13. The retrieval device of claim 10, wherein the reinforcing loop material comprises tungsten or platinum.

14. The retrieval device of claim 1, wherein the reinforcing loop material comprises PTFE.

15. The retrieval device of claim 1, further comprising a reinforcing pusher material connected to the wire proximate the proximal end of the wire.

16. The retrieval device of claim 15, wherein the reinforcing pusher material comprises nitinol.

17. The retrieval device of claim 15, wherein the reinforcing pusher material comprises stainless steel.

18. The retrieval device of claim 15, wherein the reinforcing pusher material is a second catheter, and wherein the second catheter may be manipulated to cause the portion of the wire to pass through the opening system and form the loop capable of grasping foreign bodies within the patient.

19. The retrieval device of claim 18, further comprising a first hemostasis valve connected to the distal end of the first catheter, and a second hemostasis valve connected to the distal end of the second catheter.

20. The retrieval device of claim 1, further comprising a side-arm adapter connected to the distal end of the first catheter.

21. The retrieval device of claim 20, further comprising a locking device connected to the side-arm adapter.

22. The retrieval device of claim 21, further comprising a hemostasis valve connected to the locking device.

23. A retrieval device comprising:
  a first catheter having a distal end, a proximal end, a lumen system configured to accept at least one wire such that the at least one wire may extend beyond either end of the first catheter, and an opening system through which a loop may be formed;
  a first wire configured to be placed within the lumen system and extend beyond either end of the first catheter; and
  a second wire having a distal end and a proximal end, the distal end of the second wire being attached to the first catheter;
  wherein the proximal end of the second wire may be manipulated to cause a portion of the second wire to pass through the opening system and form a loop capable of grasping foreign bodies within a patient.

24. The retrieval device of claim 23, wherein the opening system comprises two openings oriented substantially equidistant from the distal end of the first catheter.

25. The retrieval device of claim 23, wherein the loop that may be formed has an open position that is substantially circular in shape.

26. The retrieval device of claim 23, wherein the lumen system comprises a single lumen.

27. The retrieval device of claim 23, wherein the lumen system comprises a first lumen and a second lumen, and wherein the first wire is configured to be placed within the first lumen and extend beyond either end of the first catheter, and the second wire is placed within the second lumen.

28. The retrieval device of claim 23, wherein the first catheter is tapered.

29. The retrieval device of claim 23, wherein the first catheter comprises at least two segments connected together.

30. The retrieval device of claim 23, wherein the second wire is tapered.

31. The retrieval device of claim 23, further comprising a handle connected to the second wire, and wherein the handle may be manipulated to cause the portion of the second wire to pass through the opening system and form the loop capable of grasping foreign bodies within the patient.

32. The retrieval device of claim 23, further comprising a reinforcing loop material connected to the second wire such that when the proximal end of the second wire is manipulated to form the loop, at least a portion of the loop is adjacent to the reinforcing loop material.

33. The retrieval device of claim 32, further comprising a reinforcing pusher material connected to the second wire proximate the proximal end of the second wire.

34. The retrieval device of claim 33, wherein the reinforcing pusher material is a second catheter configured to accept the first wire, and wherein the second catheter may be manipulated to cause the portion of the second wire to pass through the opening system and form the loop capable of grasping foreign bodies within the patient.

35. The retrieval device of claim 34, further comprising a first hemostasis valve connected to the distal end of the first catheter, and a second hemostasis valve connected to the distal end of the second catheter.

36. The retrieval device of claim 23, further comprising a side-arm adapter connected to the distal end of the first catheter.

37. The retrieval device of claim 36, further comprising a locking device connected to the side-arm adapter.

38. The retrieval device of claim 37, further comprising a hemostasis valve connected to the locking device.

39. A method for retrieving a foreign body from a patient, comprising:
  inserting a guidewire into the patient;
  maneuvering the guidewire to an appropriate location within the patient;
  advancing a first catheter over the guidewire, the first catheter having a distal end, a proximal end, an opening system through which a loop may be formed, and a wire attached thereto, the wire being capable of forming a loop;
  manipulating the wire to capture the foreign body with the loop; and
  withdrawing the first catheter and foreign body to retrieve the foreign body from the patient.

40. The method of claim 39, wherein the opening system comprises first and second openings, the first opening being spaced from the distal end of the first catheter by a first distance, the second opening being spaced from the distal end of the first catheter by a second distance, the first and second distances being substantially equal.

41. The method of claim 39, wherein the loop that may be formed has an open position that is substantially circular in shape.

42. The method of claim 39, wherein the first catheter comprises at least two segments connected together.

43. The method of claim 39, further comprising a reinforcing loop material connected to the wire such that when the wire is manipulated to form the loop, at least a portion of the loop is adjacent to the reinforcing loop material.

44. The method of claim 39, further comprising a reinforcing pusher material connected to the wire proximate the proximal end of the wire.

45. The method of claim 44, wherein the reinforcing pusher material is a second catheter, and wherein the manipulating comprises manipulating the second catheter to capture the foreign body with the loop.

46. The method of claim 45, further comprising a first hemostasis valve connected to the distal end of the first catheter, and a second hemostasis valve connected to the distal end of the second catheter.

47. A retrieval device comprising:
- a first catheter having a distal end, a proximal end, an opening system through which a loop may be formed, the opening system positioned between the distal end and the proximal end, and a lumen system configured to accept at least (a) a guidewire such that the guidewire may extend beyond either end of the first catheter, and (b) a wire suited to forming the loop, the lumen system having an opening separate from the opening system, the opening of the lumen system configured to accept the guidewire such that the guidewire may extend beyond the distal end of the first catheter; and
- a wire having a distal end attached to the first catheter, and a proximal end;
- wherein the proximal end of the wire may be manipulated to cause a portion of the wire to form a loop external of the first catheter, the loop being capable of grasping foreign bodies within a patient.

* * * * *

UNITED STATES PATENT AND TRADEMARK OFFICE
CERTIFICATE OF CORRECTION

PATENT NO. : 6,517,550 B1
DATED : February 11, 2003
INVENTOR(S) : Konya et al.

It is certified that error appears in the above-identified patent and that said Letters Patent is hereby corrected as shown below:

Column 25,
Line 9, please delete "claim 1" and insert -- claim 10 -- therefor.

Signed and Sealed this

Twenty-fourth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,517,550 B1
DATED : February 11, 2003
INVENTOR(S) : Kónya et al.

It is certified that error appears in the above-identified patent and that said Letters Patent is hereby corrected as shown below:

<u>Column 24,</u>
Line 20, please insert -- a -- before "first catheter".

Signed and Sealed this

First Day of June, 2004

JON W. DUDAS
*Acting Director of the United States Patent and Trademark Office*